(12) United States Patent
McKernan et al.

(10) Patent No.: US 7,993,842 B2
(45) Date of Patent: Aug. 9, 2011

(54) DIRECTED ENRICHMENT OF GENOMIC DNA FOR HIGH-THROUGHPUT SEQUENCING

(75) Inventors: Kevin McKernan, Marblehead, MA (US); Alan Blanchard, Middleton, MA (US); Douglas R. Smith, Gloucester, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/504,485

(22) Filed: Jul. 16, 2009

(65) Prior Publication Data

US 2009/0280540 A1 Nov. 12, 2009

Related U.S. Application Data

(63) Continuation of application No. 11/726,719, filed on Mar. 22, 2007, now abandoned.

(60) Provisional application No. 60/785,295, filed on Mar. 23, 2006.

(51) Int. Cl.
*C12Q 1/68* (2006.01)
*C12P 19/34* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| | | |
|---|---|---|
| 5,229,273 A | 7/1993 | Gottesman et al. |
| 5,445,934 A | 8/1995 | Fodor et al. |
| 5,616,478 A | 4/1997 | Chetverin et al. |
| 5,641,658 A | 6/1997 | Adams et al. |
| 5,677,195 A | 10/1997 | Winkler et al. |
| 5,695,937 A | 12/1997 | Kinzler et al. |
| 5,705,628 A | 1/1998 | Hawkins |
| 5,744,305 A | 4/1998 | Fodor et al. |
| 5,830,663 A | 11/1998 | Embleton et al. |
| 5,866,330 A | 2/1999 | Kinzler et al. |
| 5,898,071 A | 4/1999 | Hawkins |
| 5,958,698 A | 9/1999 | Chetverin et al. |
| 6,001,568 A | 12/1999 | Chetverin et al. |
| 6,010,850 A | 1/2000 | Weissman et al. |
| 6,375,903 B1 | 4/2002 | Cerrina et al. |
| 6,383,743 B1 | 5/2002 | Kinzler et al. |
| 6,498,013 B1 | 12/2002 | Velculescu et al. |
| 6,534,262 B1 | 3/2003 | McKernan et al. |
| 7,645,866 B2 | 1/2010 | Smith et al. |
| 2002/0009729 A1 | 1/2002 | McGall et al. |
| 2004/0185484 A1 | 9/2004 | Costa et al. |

(Continued)

FOREIGN PATENT DOCUMENTS

EP 1 256 632 A2 11/2002

(Continued)

OTHER PUBLICATIONS

Adessi, C et al., "Solid Phase DNA Amplification: characterisation of primer attachment and amplification mechanisms", *Nuc Acids Research* vol. 28 (20 e87) 2000, pp. 1-8.

(Continued)

*Primary Examiner* — Young J Kim

(57) ABSTRACT

The present invention provides microarrays of oligonucleotide primer pairs, and in particular, microarrays of primers that comprise at least one cleavable linkage. Also provided are methods to capture oligonucleotide primer pairs from one or more microarrays, and methods to use the captured oligonucleotide primer pairs, such as for amplification of a target polynucleotide sequence. In addition, methods of using a microarray to isolate, purify and/or amplify a target polynucleotide are provided.

39 Claims, 7 Drawing Sheets

U.S. PATENT DOCUMENTS

| | | |
|---|---|---|
| 2005/0227263 A1 | 10/2005 | Green et al. |
| 2005/0244885 A1 | 11/2005 | Wolber et al. |
| 2005/0287585 A1 | 12/2005 | Oleinikov |
| 2006/0024681 A1 | 2/2006 | Smith et al. |
| 2006/0035218 A1 | 2/2006 | Oleinikov |
| 2006/0046251 A1 | 3/2006 | Sampson et al. |
| 2007/0026438 A1 | 2/2007 | Smith et al. |
| 2007/0172839 A1 | 7/2007 | Smith et al. |
| 2008/0286795 A1 | 11/2008 | Kawashima et al. |

FOREIGN PATENT DOCUMENTS

| | | |
|---|---|---|
| EP | 1 518 937 A1 | 3/2005 |
| WO | WO-91/07486 | 5/1991 |
| WO | WO-00/18957 | 4/2000 |
| WO | WO-00/53812 | 9/2000 |
| WO | WO 2004/069849 A2 | 8/2004 |
| WO | WO 2005/010145 A2 | 2/2005 |
| WO | WO 2005/065814 A1 | 7/2005 |
| WO | WO 2007/002890 A2 | 1/2007 |
| WO | WO 2007/087291 A2 | 1/2007 |

OTHER PUBLICATIONS

Nuwaysir, E et al., "Gene Expression Analysis Using Oligonucleotide Arrays Produced by Maskless Photolithography", *Genome Research* 2002, pp. 1749-1755.

PCT/US2007/007112, "International Search Report", Aug. 1, 2007, pp. 1-3.

Raghavendra, N et al., "Exogenous AdoMet and its analogue sinefungin differentially influence DNA cleavage by R.EcoP15I—Usefulness in SAGE", *Biochem and Biophysical Research Communications* 334 2005, pp. 803-811.

Tucholski, J et al., "Two intertwined methylation activities of MmeI restriction-modification class-IIS system from Methylophilus methylotrophus", *Gene* 223 1998, pp. 290-302.

Butz, J., et al., "Characterization of Mutations and Loss of Heterozygosity of p53 and K-*ras*2 in Pancreatic Cancer Cell Lines by Immobilized Polymerase Chain Reaction," *BMC Biotechnol.*, 3(11)(2003). [online] Retrieved from the Internet <URL: http://www.biomedcentral.com/1472-6750/3/11>.

Butz, J.A., et al., "Detection of Allelic Variations of Human Gene Expression by Polymerase Colonies," *BMC Genet.* 5(3)(2004). [online] Retrieved from the Internet <URL: http://www.biomedcentral.com/1471-2156/5/3>.

Dahl, F., et al., "Multiplex Amplification Enabled by Selective Circularization of Large Sets of Genomic DNA Fragments," *Nucleic Acids Res.*, 33(8) (2005).

Dressman, D., et al., "Transforming Single DNA Molecules into Fluorescent Magnetic Particles for Detection and Enumeration of Genetic Variations," *Proc. Natl. Acad. Sci. USA*, 100(15): 8817-8822 (2003).

Jiang, D., et al., "Characterization of *Escherichia coli* Endonuclease VIII," *J. Biol. Chem.*, 272(51): 32230-32239 (1997).

Kwiatkowski, M., et al., "Inversion of In Situ for Synthesized Oligonucleotides: Improved Reagents for Hybridization and Primer Extension in DNA Microarrays," *Nucleic Acids Res.*, 27(24): 4710-4714 (1999).

Lindahl, T., et al., "DNA N-Glycosidases: Properties of Uracil—DNA Glycosidase from *Escherichia coli*," *J. Biol. Chem.*, 252(10): 3286-3294 (1977).

Lindahl, T., "DNA Repair Enzymes," *Annu. Rev. Biochem.*, 51: 61-64 (1982).

Mag, M., et al., "Synthesis and Selective Cleavage of an Oligodeoxynucleotide Containing a Bridged Internucleotide 5'-phosphorathioate Linkage," *Nucleic Acids Res.*, 19(7):1437-1441 (1991).

Melamede, R.J., et al., "Isolation and Characterization of Endonuclease VIII from *Escherichia coli*," *Biochem.*, 33: 1255-1264 (1994).

Mitra, R.D. and Church, G.M., "In Situ Localized Amplification and Contact Replication of Many Individual DNA Molecules," *Nucleic Acids Res.*, 27(24) (1999).

Mitra, R.D., et al., "Digital Genotyping and Haplotyping with Polymerase Colonies," *Proc. Natl. Acad. Sci. USA*, 100(10): 5926-5931 (2003).

Shendure, J., et al., "Accurate Multiplex Polony Sequencing of an Evolved Bacterial Genome," *Science*, 309:1728-1732 (2005).

Sontheimer, E.J., "Bridging Sulfur Substitutions in the Analysis of Pre-mRNA Splicing," *Methods*, 18: 29-37 (1999).

Velculescu, V.E., et al., "Serial Analysis of Gene Expression," *Science*, 270(5235): 484-487 (1995).

Vyle, J.S., et al., "Sequence- and Strand-Specific Cleavage in Oligodeoxyribonucleotides and DNA Containing 3'-Thiothymidine," *Biochem.*, 31: 3012-3018 (1992).

Wang, T.-L., et al., "Digital Karyotyping," *Proc. Natl. Acad. Sci. USA*, 99(25):16156-16161 (2002).

Bentley, D et al., Accurate whole human genome sequencing using reversible terminator chemistry, Nature, Supplementary Information, pp. 1-55 (2008).

Bentley, D et al., Accurate whole human genome sequencing using reversible terminator chemistry, Nature, vol. 456(6), pp. 53-59 (2008).

Chiu, K-P et al., Intracellular Amplification of Proviral DNA in Tissue Sections Using the Polymerase Chain Reaction, J. Histochemistry and Cytochemistry, vol. 40(3), pp. 333-341 (1992).

Quail, M. et al., Improved Protocols for the Illumina Genome Analyzer Sequencing System, Current Protocols in Human Genetics, Supplement 62, John Wiley & Sons, Inc., Unit 18.2.1-18.2.27 (2009).

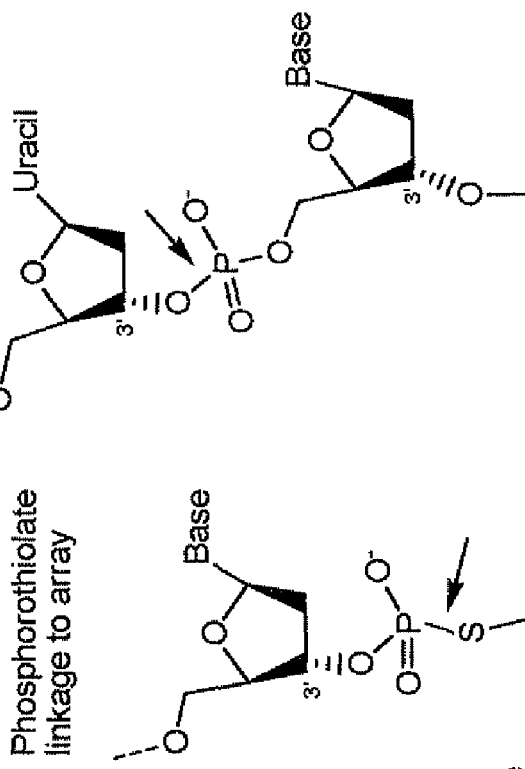
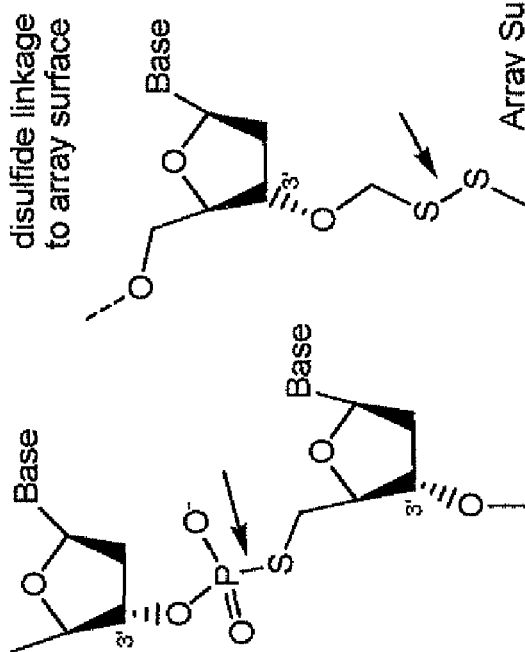

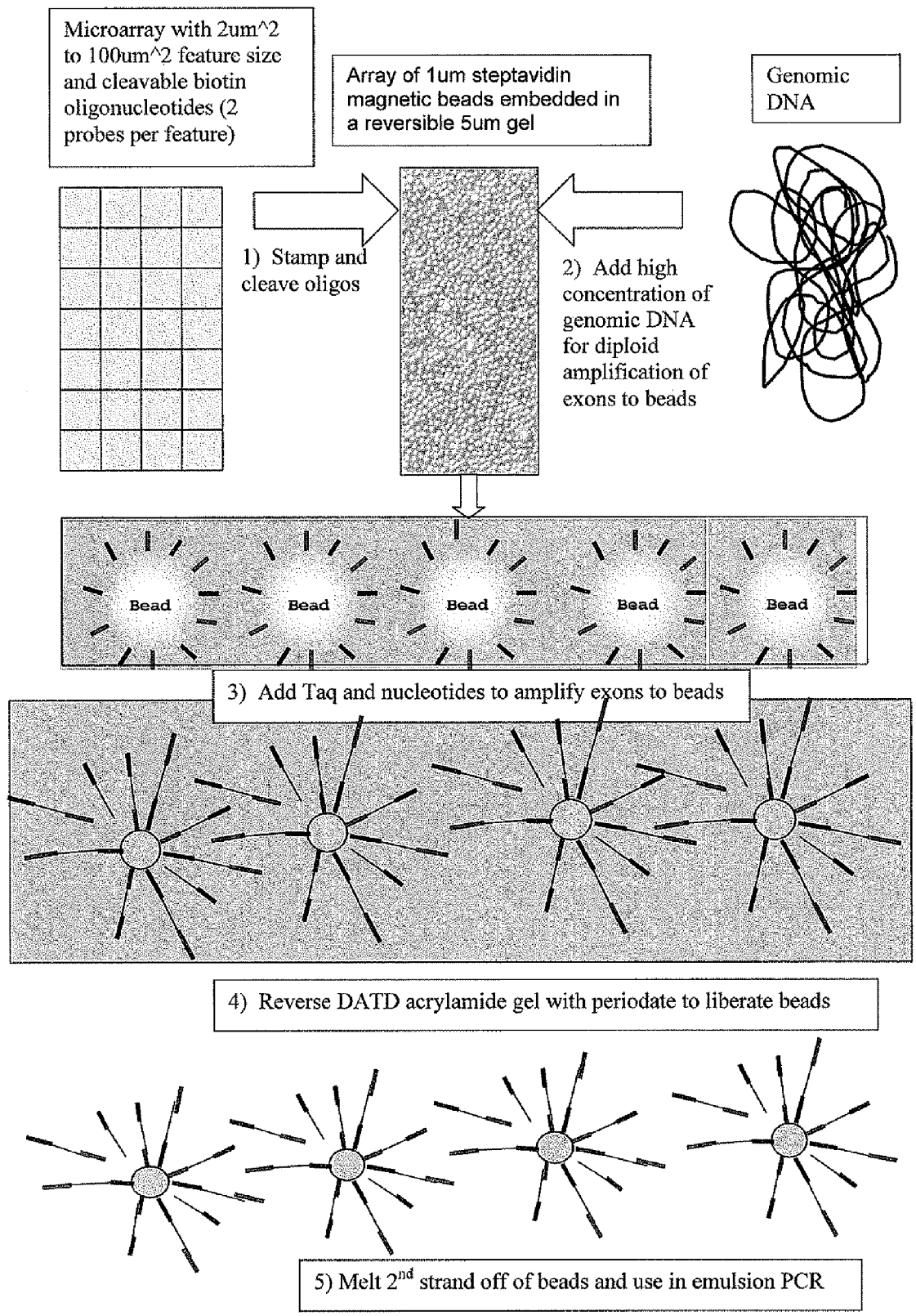

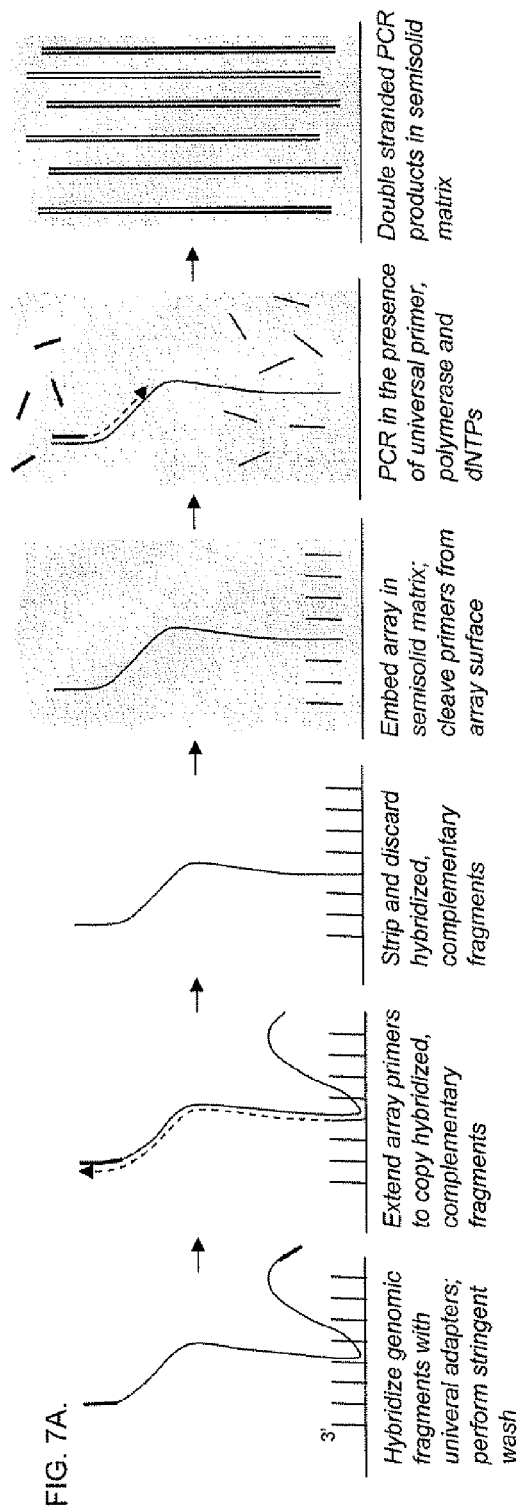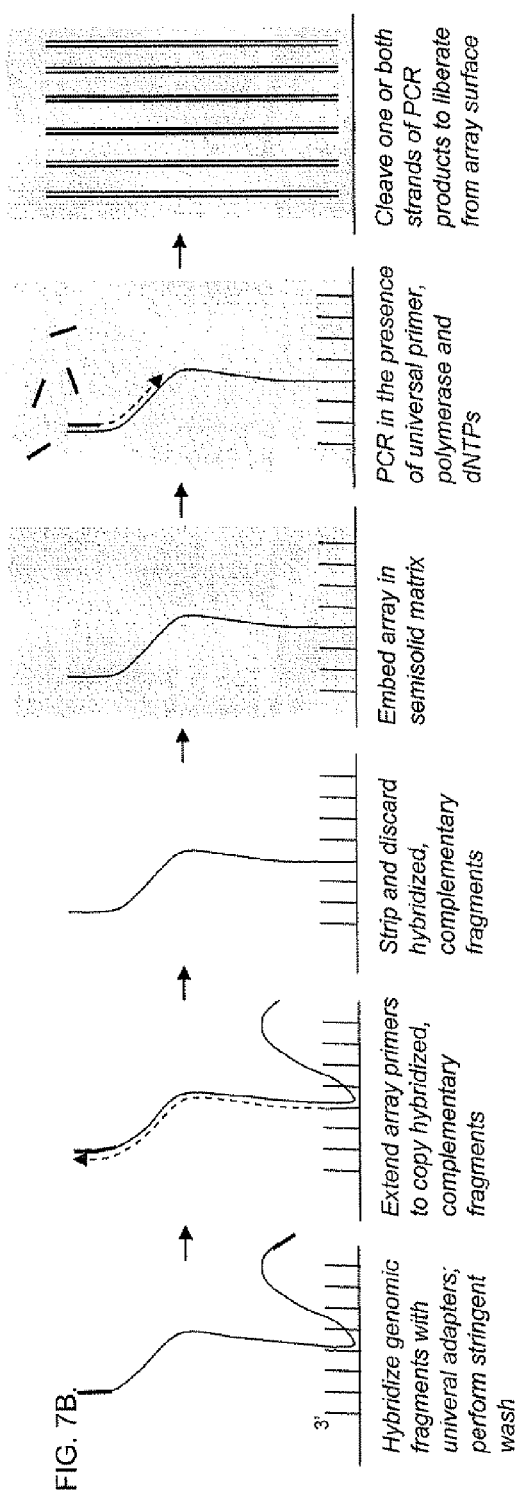

DIRECTED ENRICHMENT OF GENOMIC DNA FOR HIGH-THROUGHPUT SEQUENCING

RELATED APPLICATION

This application is a continuation of application Ser. No. 11/726,719, filed on Mar. 22, 2007, and claims the benefit of U.S. Provisional Application No. 60/785,295, filed on Mar. 23, 2006. The entire teachings of the above applications are incorporated herein by reference.

BACKGROUND OF THE INVENTION

Large numbers of amplicons or polymerase chain reaction products (PCR) products are necessary to amplify every exon in a genome. For example, the amplification all of the exons in the human genome would require approximately 250,000 amplicons or PCR products. For each amplicon, a pair of primers needs to be synthesized and an individual PCR reaction needs to be carried out, which is a costly and unwieldy task for the total number of 250,000 amplicons required to sequence all of the exons in the human genome.

Microarray technologies are available that can synthesize very small quantities of up to about 400,000 oligonucleotides on a single solid support. These 400,000 oligonucleotides could potentially comprise 200,000 primer pairs for an amplification reaction, such as PCR. All 400,000 oligonucleotides can be liberated from the microarray into a single (multiplex) PCR reaction using known methods. However, the resulting multiplex PCR using these 200,000 primer pairs in one reaction is likely to be uninformative due to the complexity of the reaction and due to numerous artifacts, such as primer-dimer formation. There is currently no known method to segregate individual primers pairs from a microarray into individual PCR reactions.

Thus, a need exists to segregate primer pairs from a microarray, such that individual primer pairs can be used, for example, in an amplification reaction.

SUMMARY OF THE INVENTION

The present invention provides microarrays of oligonucleotides, e.g., primer pairs, and in particular, microarrays of primers that comprise at least one cleavable linkage. Also provided are methods to capture oligonucleotide primer pairs from one or more microarrays, and methods to use the captured oligonucleotide primer pairs, such as for amplification of a target polynucleotide sequence. In addition, methods of using a microarray to isolate, purify and/or amplify a target polynucleotide are provided.

Present microarray technologies can synthesize very small quantities of up to about 400,000 oligonucleotides on a single solid support. Therefore, these 400,000 oligonucleotides can theoretically comprise around 200,000 primer pairs for amplifying one or more target polynucleotides in an amplification reaction, such as PCR. However, there is no current method to separate the 200,000 primer pairs into 200,000 separate amplification reactions. Although all 400,000 oligonucleotides can be liberated from the microarray into a single (multiplex) PCR reaction using known methods, the resulting multiplex PCR reaction has little informative value due to the complexity of the amplified products generated and due to numerous artifacts that result from such a multiplex PCR, such as primer-dimer formation (see, e.g., Dahl et al., Nuc. Ac. Res. (2005), 33(8): e71, and references cited therein).

There is a need for methods to segregate primer pairs from a microarray, and methods of using such primer pairs, for example, in one or more amplification reactions. Thus, the present invention provides microarrays comprising primer pairs that can be used in methods of segregating and/or capturing primer pairs from the microarrays such that the primer pairs, for example, can amplify a target polynucleotide in one or more separate amplification reactions.

The present invention provides a microarray comprising a plurality of oligonucleotide primer pairs, wherein each oligonucleotide primer pair comprises a first oligonucleotide primer and a second oligonucleotide primer. Each primer comprises at least one cleavable linkage for releasing the primer from the microarray. Thus, cleaving the cleavable linkage in each primer will release the plurality of oligonucleotide primer pairs from the microarray.

The present invention also provides a microarray comprising a plurality of oligonucleotides in which each oligonucleotide comprises (a) two primer nucleic acid sequences; (b) a first cleavable linkage which is located at or near the microarray surface, such that cleaving the first cleavable linkage separates each oligonucleotide from the microarray surface; and (c) a second cleavable linkage located between the two primer nucleic acid sequences in each oligonucleotide, such that cleaving the second cleavable linkage separates the two primer nucleic acid sequences. In one embodiment, the two primer nucleic acid sequences are a primer pair.

Also provided herein is a method for producing a microarray, such that a plurality of oligonucleotide primer pairs are synthesized on the microarray. Each oligonucleotide primer pair when synthesized is present at a discrete location (also referred to herein as a "feature" or an "element") on the microarray and comprises a first primer and a second primer. The first primer and second primer each comprise at least one cleavable linkage. The method comprises providing a microarray which comprises a plurality of discrete locations, and each discrete location comprises a first primer synthesis site and a second primer synthesis site. Each second primer synthesis site is capped with a blocking group to prevent primer synthesis at the second primer synthesis site. The first primers comprising at least one cleavable linkage are synthesized at each first primer synthesis site on the microarray, which produces a plurality of first primers on the microarray. The method further comprises capping the plurality of first primers to prevent further synthesis of each first primer. Each second primer synthesis site is uncapped and a second primer comprising at least one cleavable linkage is synthesized at each second primer synthesis site on the microarray, which produces a plurality of second primers on the microarray. Thus, the method produces a microarray, wherein a plurality of oligonucleotide primer pairs are synthesized on the microarray. Also provided in the present invention is a microarray produced by the described method.

Another aspect of the present invention is a method for capturing a plurality of oligonucleotide primer pairs on a capturing means in a capturing support, wherein each oligonucleotide primer pair is present at a discrete location on the capturing support. In a particular embodiment, the primer pairs are located at a discrete location on a microarray and the discrete locations of the primer pairs are maintained when the primer pairs are captured on a capturing support, wherein each discrete location comprises or consists essentially of one primer pair. In one embodiment, a plurality of discrete locations comprises a plurality of primer pairs, wherein each discrete location comprises or consists essentially of one primer pair, and wherein each primer pair is the same or different. Each oligonucleotide primer of each primer pair comprises at least one first cleavable linkage and the capturing support comprises a capturing means for capturing the oligonucleotide primer pairs. The method comprises capturing or transferring (e.g., embedding) each oligonucleotide primer pair present at a discrete location on a microarray into a capturing support, capturing the oligonucleotide primer pairs on the microarray by the capturing means and separating the oligonucleotide primer pairs from the microarray by cleaving the at least one first cleavable linkage in each oligonucleotide primer, thereby capturing a plurality of oligonucleotide primer pairs on a capturing means in a capturing support, wherein each oligonucleotide primer pair is present at a discrete location on the capturing support. The method can further comprise separating the capturing means from the capturing support, thereby producing a plurality of capturing means, wherein at least a portion of the capturing means comprise an oligonucleotide primer pair.

The present invention also provides a method for capturing a plurality of oligonucleotide primer pairs from two microarrays and the primer pairs are captured on a capturing support. Each oligonucleotide primer pair comprises a first primer that is located on a first microarray at a discrete location and a second primer that is located on the second microarray at a discrete location. Each first primer is captured from a first microarray and each second primer is captured from a second microarray. Each primer also comprises at least one cleavable linkage to separate the primer from the microarray. The method comprises embedding a first microarray comprising a plurality of first primers into a capturing support under conditions in which each of the first primers are captured in the capturing support and the discrete location of each of the first primers is maintained in the capturing support. The method further comprises separating the first primers from the first microarray by cleaving the at least one cleavable linkage in the first primers and removing the first microarray from the capturing support. Upon removal of the first microarray, the first primers remain in the discrete locations in the capturing support. In addition, the method comprises embedding a second microarray comprising a plurality of second primers into the capturing support under conditions in which each of the second primers are captured in the capturing support and the discrete location of each of the second primers is maintained in the capturing support, and the discrete location of each of the second primers overlaps with the discrete location of each of the first primers. When the discrete location of the first primer and second primer overlap in the capturing support, each discrete location in the capturing support comprises or consists essentially of a primer pair that can be used in an amplification reaction. The method also comprises separating the second primers from the second microarray by cleaving the at least one cleavable linkage in each of the second primers. Thus, the method captures a plurality of oligonucleotide primer pairs on a capturing support, wherein each oligonucleotide primer pair comprises a first primer and a second primer, and wherein each first primer is captured from a first microarray and each second primer is captured from a second microarray.

Another aspect of the invention is a method for amplifying a target polynucleotide using oligonucleotide primer pairs wherein each oligonucleotide primer pair is located at a discrete position on a microarray. Each primer in each oligonucleotide primer pair comprise at least one cleavable linkage. The method comprises providing a plurality of oligonucleotide primer pairs, wherein each oligonucleotide primer pair is located at a discrete position on a microarray. A target polynucleotide is hybridized to at least one primer in at least one oligonucleotide primer pair on the microarray, to produce a microarray comprising at least one primer pair comprising at least one primer hybridized to a target polynucleotide. The microarray is embedded into a capturing support (e.g., by coating the microarray with a semisolid matrix). The at least one primer oligonucleotide pair comprising at least one primer hybridized to a target polynucleotide is separated from the microarray (e.g., liberated from the microarray surface) by cleaving the at least one cleavable linkage in each primer to release the at least one oligonucleotide primer pair comprising at least one primer hybridized to a target polynucleotide from the microarray, wherein the at least one oligonucleotide primer pair comprising at least one primer hybridized to a target polynucleotide is captured in the capturing support. The method further comprises amplifying the target polynucleotide under conditions in which the at least one oligonucleotide primer pair comprising at least one primer hybridized to the target polynucleotide amplifies the target polynucleotide by polymerase chain reaction, such that an amplified target polynucleotide is produced.

In one embodiment, the oligonucleotide primers are synthesized on the microarray in the conventional 3'-down orientation. In another embodiment, the oligonucleotide primers are synthesized in the 5'-down orientation.

In a particular embodiment, a target polynucleotide hybridized to an oligonucleotide primer on the array is copied by extension of the 3' hydroxyl of one oligonucleotide primer using DNA polymerase and deoxynucleoside triphosphates. The hybridized target polynucleotide can be released by chemical or thermal denaturation and discarded before proceeding with the embedding in a capturing support, or alternatively, the double-stranded primer extension product is cleaved after embedding in a capturing support by treatment with a restriction endonuclease.

In a particular embodiment, each oligonucleotide primer further comprises at its 5' end a restriction endonuclease recognition site for a distally cleaving restriction endonuclease. Thus, in one embodiment, the method further comprises cleaving the amplified target polynucleotide with a restriction endonuclease specific for the restriction endonuclease recognition site, which produces a fragment of the amplified target polynucleotide, such that at least a portion of the oligonucleotide primer sequence is removed. In a further embodiment, the method further comprises joining a pair of sequencing adapters to the fragment of the amplified target polynucleotide, such that one sequencing adapter is joined to each end of the fragment, and each sequencing adapter comprises a primer binding site. This produces an adapter-modified target polynucleotide. In a particular embodiment, the adapter-modified target polynucleotide is sequenced. In another particular embodiment, the sequencing adapters that are joined to the fragment of the amplified target polynucleotide are a pair of asymmetrical adapters. In one embodiment, the pair of sequencing adapters is a pair of asymmetrical adapters. In a particular embodiment, the pair of asymmetrical adapters comprise:

a) a first oligonucleotide adapter selected from the group consisting of:
  (i) an asymmetrical tail adapter comprising a first ligatable end, and a second end comprising a single-stranded 3' overhang of at least about 8 nucleotides;
  (ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;
and
a second oligonucleotide adapter selected from the group consisting of:
(iv) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
(v) an asymmetrical Y adapter comprising a first ligatable end, and a second unpaired end comprising two non-complementary strands, wherein the length of the non-complementary strands are at least about 8 nucleotides;
(vi) and
(vii) an asymmetrical bubble adapter comprising an unpaired region of at least about 8 nucleotides flanked on each side by a paired region;
wherein the nucleic acid sequence of the first and second asymmetrical adapters are not identical.

In an alternative embodiment, the method for amplifying a target polynucleotide further comprises joining a universal adapter to each end of the amplified target polynucleotide to produce a first adapter-modified target polynucleotide. Each universal adapter comprises a primer binding site, and the 3' end of each universal adapter comprises a restriction endonuclease recognition site for a distally cleaving restriction endonuclease. In one embodiment, the method further comprises amplifying the first adapter-modified target polynucleotide to produce an amplified adapter-modified target polynucleotide. In a further embodiment, the method further comprises cleaving the amplified adapter-modified target polynucleotide with a restriction endonuclease specific for the restriction endonuclease recognition site, which produces a fragment of the amplified adapter-modified target polynucleotide, such that at least a portion of the universal adapter sequence is removed. In a still further embodiment, the method further comprises joining a pair of sequencing adapters to the fragment of the amplified adapter-modified target polynucleotide to produce a second adapter-modified target polynucleotide, such that one sequencing adapter is joined to each end of the fragment, and each sequencing adapter comprises a primer binding site. In a particular embodiment, the second adapter-modified target polynucleotide is sequenced. In a further particular embodiment, the sequencing adapters are a pair of asymmetrical adapters. In one embodiment, the pair of asymmetrical adapters comprise:

a) a first oligonucleotide adapter selected from the group consisting of:
(i) an asymmetrical tail adapter comprising a first ligatable end, and a second end comprising a single-stranded 3' overhang of at least about 8 nucleotides;
(ii) an asymmetrical Y adapter comprising a first ligatable end, and a second unpaired end comprising two non-complementary strands, wherein the length of the non-complementary strands are at least about 8 nucleotides;
and
(iii) an asymmetrical bubble adapter comprising an unpaired region of at least about 8 nucleotides flanked on each side by a paired region;
and
a second oligonucleotide adapter selected from the group consisting of:
(iv) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
(v) an asymmetrical Y adapter comprising a first ligatable end, and a second unpaired end comprising two non-complementary strands, wherein the length of the non-complementary strands are at least about 8 nucleotides;
(vi) and
(vii) an asymmetrical bubble adapter comprising an unpaired region of at least about 8 nucleotides flanked on each side by a paired region;
wherein the nucleic acid sequence of the first and second asymmetrical adapters are not identical.

In a further alternative embodiment of the method for amplifying a target polynucleotide, each oligonucleotide primer further comprises a restriction endonuclease recognition site for a distally cleaving restriction endonuclease, and at least one oligonucleotide primer in the oligonucleotide primer pair further comprises a universal primer sequence. In a particular embodiment, the capturing support further comprises a primer that is identical to the universal primer sequence in the at least one oligonucleotide primer. In one embodiment, the primer that is identical to the universal primer sequence further comprises a moiety that can be co-polymerized with a polyacrylamide gel, e.g., a moiety selected from the group consisting of acrylamide, acrylic acid and vinyl. In a further embodiment, the method further comprises amplifying the target polynucleotide under conditions in which at least one oligonucleotide primer and the primer that is identical to the universal primer sequence amplifies the target polynucleotide by polymerase chain reaction, thereby producing an amplified target polynucleotide. In a particular embodiment, the method further comprises cleaving the amplified target polynucleotide with a restriction endonuclease specific for the restriction endonuclease recognition site to produce a fragment of the amplified target polynucleotide, wherein at least a portion of the oligonucleotide primer sequences are removed. In a further embodiment, the method further comprises joining a pair of sequencing adapters to the fragment of the amplified target polynucleotide to produce an adapter-modified target polynucleotide, such that one sequencing adapter is joined to each end of the fragment. Each sequencing adapter comprises a primer binding site. In one embodiment, the adapter-modified target polynucleotide is sequenced. In a particular embodiment, the pair of sequencing adapters is a pair of asymmetrical adapters. In one embodiment, the pair of asymmetrical adapters comprise:

a) a first oligonucleotide adapter selected from the group consisting of:
(i) an asymmetrical tail adapter comprising a first ligatable end, and a second end comprising a single-stranded 3' overhang of at least about 8 nucleotides;
(ii) an asymmetrical Y adapter comprising a first ligatable end, and a second unpaired end comprising two non-complementary strands, wherein the length of the non-complementary strands are at least about 8 nucleotides;
and
(iii) an asymmetrical bubble adapter comprising an unpaired region of at least about 8 nucleotides flanked on each side by a paired region;
and
a second oligonucleotide adapter selected from the group consisting of:
(iv) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;

(v) an asymmetrical Y adapter comprising a first ligatable end, and a second unpaired end comprising two non-complementary strands, wherein the length of the non-complementary strands are at least about 8 nucleotides; and (vi) an asymmetrical bubble adapter comprising an unpaired region of at least about 8 nucleotides flanked on each side by a paired region;

wherein the nucleic acid sequence of the first and second asymmetrical adapters are not identical.

In a still further particular embodiment, the method for amplifying a target polynucleotide further comprises joining to the ends of the amplified target polynucleotide a pair of asymmetrical adapters. In one embodiment, the pair of asymmetrical adapters comprise:

a) a first oligonucleotide adapter selected from the group consisting of:

(i) an asymmetrical tail adapter comprising a first ligatable end, and a second end comprising a single-stranded 3' overhang of at least about 8 nucleotides;

(ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

and a second oligonucleotide adapter selected from the group consisting of:

(iv) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;

(v) an asymmetrical Y adapter comprising a first ligatable end, and a second unpaired end comprising two non-complementary strands, wherein the length of the non-complementary strands are at least about 8 nucleotides; and (vi) an asymmetrical bubble adapter comprising an unpaired region of at least about 8 nucleotides flanked on each side by a paired region;

wherein the first and second asymmetrical adapters further comprise a restriction endonuclease recognition site for a distally cleaving restriction endonuclease, and the nucleic acid sequence of the first and second asymmetrical adapters are not identical. Joining the pair of asymmetrical adapters to the ends of the amplified target polynucleotide produces a first adapter-modified target polynucleotide. In a particular embodiment, the method further comprises amplifying the first adapter-modified target polynucleotide to produce an amplified adapter-modified target polynucleotide. In one embodiment, the amplified adapter-modified target polynucleotide is cleaved with a restriction endonuclease specific for the restriction endonuclease recognition site to produce a fragment of the amplified adapter-modified target polynucleotide, wherein at least a portion of the asymmetrical adapter sequences are removed. In a further embodiment, the method further comprises joining a pair of sequencing adapters to the fragment of the amplified adapter-modified target polynucleotide to produce a second adapter-modified target polynucleotide, such that one sequencing adapter is joined to each end of the fragment and each sequencing adapter comprises a primer binding site. In one embodiment, the second adapter-modified target polynucleotide is sequenced. In a particular embodiment, the pair of sequencing adapters is a pair of asymmetrical adapters. In one embodiment, the pair of asymmetrical adapters comprise:

b) a first oligonucleotide adapter selected from the group consisting of:

(i) an asymmetrical tail adapter comprising a first ligatable end, and a second end comprising a single-stranded 3' overhang of at least about 8 nucleotides;

(ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

and a second oligonucleotide adapter selected from the group consisting of:

(iv) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;

(v) an asymmetrical Y adapter comprising a first ligatable end, and a second unpaired end comprising two non-complementary strands, wherein the length of the non-complementary strands are at least about 8 nucleotides; and (vi) an asymmetrical bubble adapter comprising an unpaired region of at least about 8 nucleotides flanked on each side by a paired region;

wherein the nucleic acid sequence of the first and second asymmetrical adapters are not identical.

In another embodiment of the invention, provided is a method for amplifying a target polynucleotide (see FIGS. 7A-7B). The method comprises providing an oligonucleotide primer located at a discrete position on a microarray, wherein the oligonucleotide primer comprises at least one cleavable linkage. A target polynucleotide is hybridized to the oligonucleotide primer on the microarray, wherein the target polynucleotide comprises a universal adapter ligated to each end of the target polynucleotide. Each universal adapter comprises a universal primer sequence. After hybridization, a microarray comprising an oligonucleotide primer hybridized to a target polynucleotide is produced. The oligonucleotide primer hybridized to the target polynucleotide is extended under appropriate condition to produce a first strand primer extension product, which is located at a discrete location on the microarray because the oligonucleotide primer was located at the discrete location on the microarray. The method further comprises removing the target polynucleotide from the first strand primer extension product, thereby leaving the first strand primer extension product located at a discrete location on the microarray. The first strand primer extension product located at a discrete location on the microarray is embedded into a capturing support, wherein the capturing support comprises a universal primer. The universal primer binds to a universal primer binding site located in the first strand extension product as a result of primer extension of the universal adapter sequence on the target polynucleotide. The target polynucleotide is amplified in the capturing support under conditions in which the oligonucleotide primer hybridized to the target polynucleotide and the universal primer amplifies the target polynucleotide by polymerase chain reaction, whereby an amplified target polynucleotide is produced, and thereby amplifying the target polynucleotide.

In one embodiment, the oligonucleotide primer on the microarray is cleaved before amplifying the target polynucleotide in the capturing support to release the oligonucleotide primer from the microarray before amplification (see FIG. 7A). In an alternative embodiment, the method further comprises cleaving the oligonucleotide primer on the microarray after amplifying the target polynucleotide in the capturing support to release the amplified target polynucleotide from the microarray (see FIG. 7B). In another embodiment, the oligonucleotide primer further comprises a restriction endonuclease recognition site for a distally cleaving restriction endonuclease. For example, the distally cleaving restriction endonuclease is a Type IIs or a Type III restriction endonuclease. Thus, in one embodiment, the method comprises cleaving the oligonucleotide primer with a restriction endonuclease specific for the restriction endonuclease recognition site after amplifying the target polynucleotide in the capturing support. After cleavage, a fragment of the amplified target polynucleotide is produced. In a preferred embodiment, at least a portion of the oligonucleotide primer sequence is removed after cleavage with a restriction endonuclease recognition site for a distally cleaving restriction endonuclease.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D are schematics of a microarray surface with four examples of oligonucleotide cleavable linkages. These cleavable linkages can be cleaved under mild conditions. The position of the cleavage is indicated by an arrow. FIG. 1A illustrates a 5' phosphorothiolate linkage. FIG. 1B illustrates a disulfide linkage (bond). FIG. 1C illustrates a 3' phosphorothiolate linkage. FIG. 1D illustrates a deoxyuridine linkage.

FIG. 2 is a schematic representation of one embodiment of the present invention. A microarray of oligonucleotides with at least one cleavable linkage and an affinity tag (e.g., biotin) is embedded ("stamped") into a capturing support comprising a capturing means (e.g., a reversible polyacrylamide gel comprising streptavidin magnetic beads). The target polynucleotide (e.g., genomic DNA) is added to the oligonucleotide array that is embedded into the capturing support, and a nucleotide sequence (e.g., an exon) of the genomic DNA is amplified in an amplification reaction (e.g., polymerase chain reaction (PCR)). The magnetic beads comprising the amplified target polynucleotide is released ("liberated") from the reversible polyacrylamide (e.g., by using periodate). One strand of the amplified target polynucleotide is separated from the magnetic bead by disassociating (e.g., "melting" or denaturation) a double-stranded amplified target polynucleotide using e.g., temperature change. The separated strand can be further amplified e.g., in an emulsion PCR reaction.

FIGS. 7A-7B are schematic representation of embodiments of the invention.

DETAILED DESCRIPTION OF THE INVENTION

Figure 3:
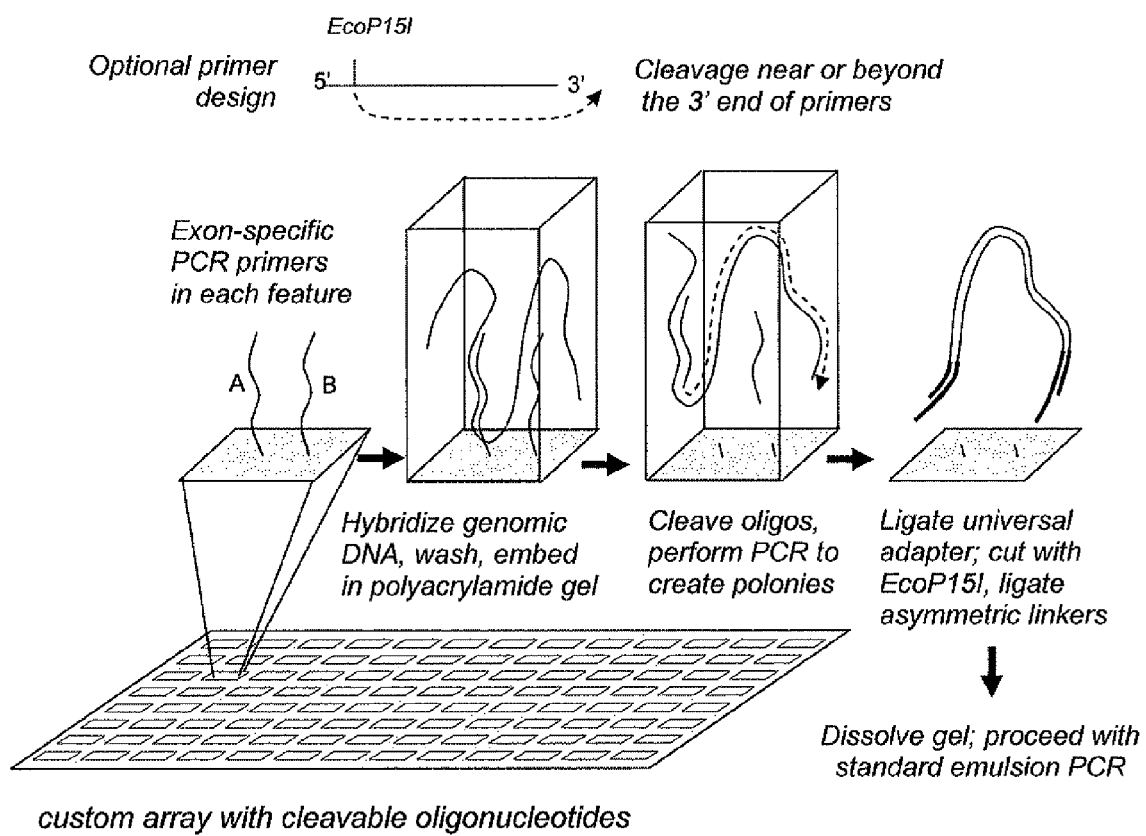
FIG. 3 is schematic representation of another embodiment of the present invention. In this embodiment, target polynucleotides are amplified on a microarray (e.g., by polony PCR), and the amplified target nucleic acid sequences are joined to sequencing adapters (e.g., asymmetrical adapters) for further amplification (e.g., in an emulsion PCR).
Figure 4:
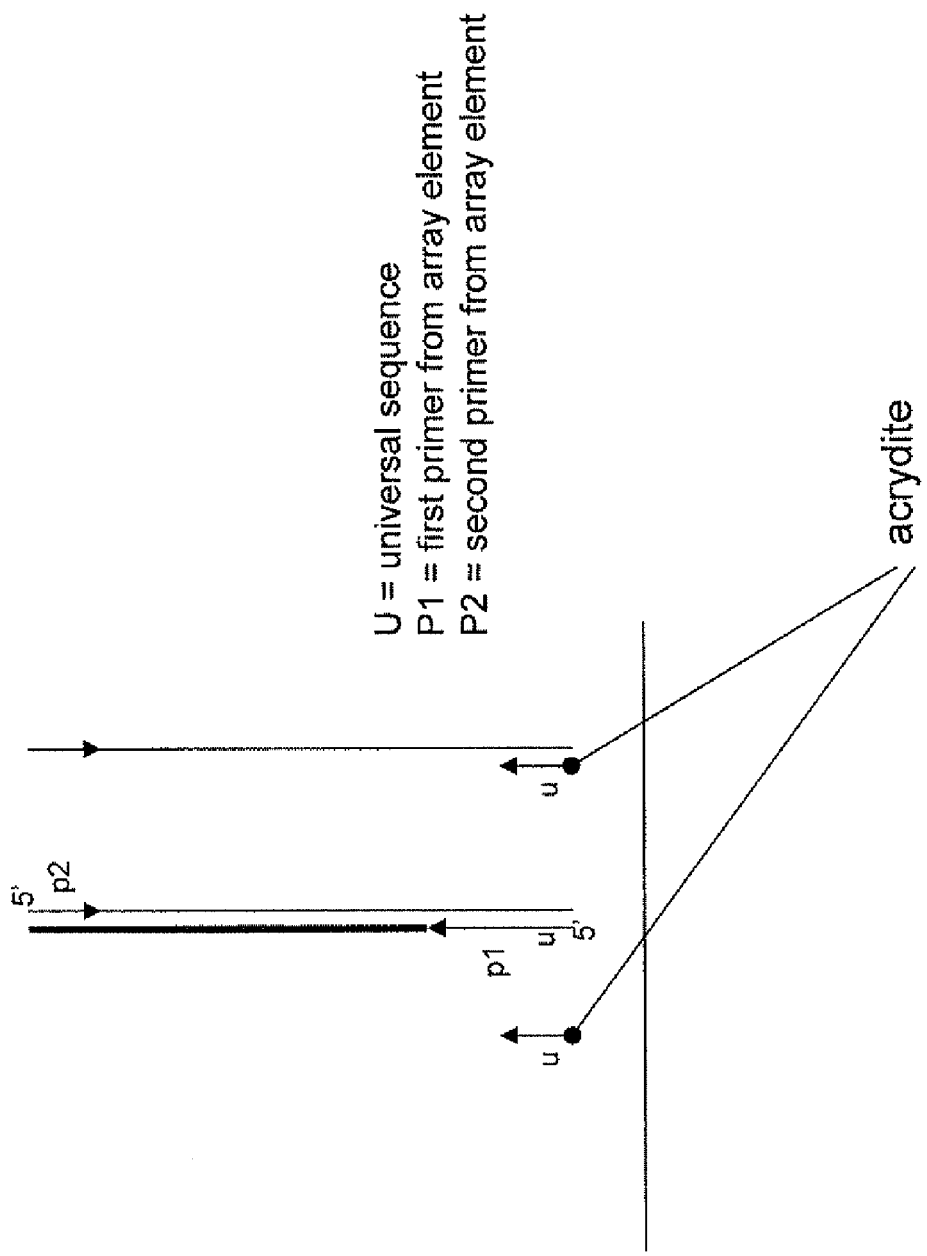
FIG. 4 is a schematic representation of one embodiment of the invention wherein a microarray comprises an oligonucleotide primer pair, P1 and P2. At least one primer (e.g., P1) comprises a universal nucleic acid sequence. A third primer comprises the universal nucleic acid sequence. In one embodiment, a capturing support comprises the third primer. In this example, the third primer can further comprise an acrylamide group (e.g., ACRYDITE™). Amplification of the target polynucleotide is performed with the two primers from the microarray and the universal primer.
Figure 5:
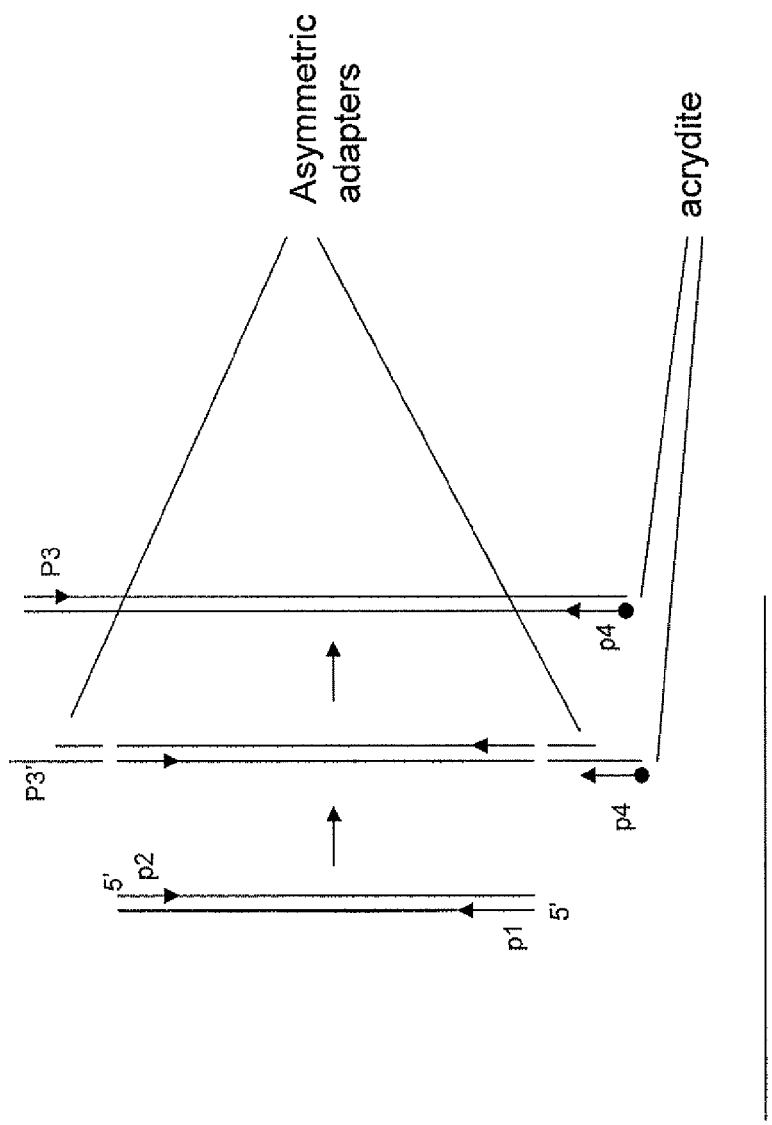
FIG. 5 is a schematic representation of one embodiment of the invention. A target polynucleotide is amplified in an amplification reaction (e.g., polony PCR) comprising two oligonucleotide primers from a microarray. The amplified target nucleic acid sequences are joined to a pair of asymmetrical adapters to produce adapter-modified target nucleic acid sequences, which can be further amplified in an amplification reaction comprising a third primer (e.g., P3) that is complementary to at least a portion of a first primer binding site in one asymmetrical adapter and a primer (e.g., P4) that is complementary to a second primer binding site of a first nucleic acid strand that is synthesized by the third primer in the amplification reaction.
Figure 6:
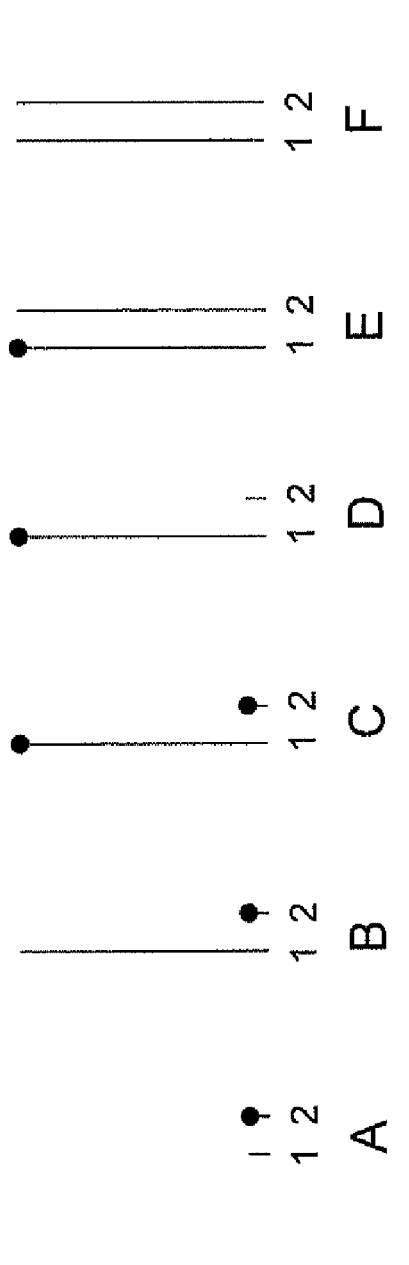
FIG. 6 is a schematic representation of a method comprising steps A through F for synthesizing an oligonucleotide primer pair at a discrete location (feature) on a microarray. The method can be performed at multiple locations on a microarray (either simultaneously or sequentially) to produce a plurality of oligonucleotide primer pairs, wherein each primer pair is at a discrete location on the microarray.

Amplifying all of the exons in the human genome requires 250,000 amplicons or polymerase chain reaction (PCR) products. Manufacturing the required 250,000 primer pairs is a challenging task. Microarray technologies offer an attractive approach for the synthesis of very small quantities of up to 400,000 oligonucleotides on a single solid support. However, liberating or releasing these 400,000 oligonucleotides from the microarray for use as amplification primers (e.g., for PCR) has not been useful because there is no current method for segregating the appropriate primer pairs into individual amplification reactions. It is known that all 400,000 oligonucleotides can be released into a single PCR amplification reaction. But, the resulting multiplex PCR reaction has little informative value due to the complexity of the amplified products generated and due to numerous artifacts that result from such a multiplex PCR, such as primer-dimer formation. Thus, there is a need for methods to segregate primer pairs from a microarray, and methods of using such primer pairs, for example, in one or more amplification reactions.

The present invention provides microarrays and methods of segregating and/or capturing oligonucleotides, and in particular, primer pairs from the microarrays. Such primer pairs can be used, for example, to amplify a target polynucleotide in one or more separate amplification reactions.

As used herein, an "oligonucleotide" refers to a polynucleotide sequence, such as a primer, a probe and the like. As used herein, a "primer" refers to an oligonucleotide that can hybridize (also referred to herein as "anneal") to a template polynucleotide sequence and initiate synthesis of a polynucleotide that is complementary to the template polynucleotide sequence. A primer pair (also referred to herein as an "oligonucleotide primer pair") is a pair of primers that together can amplify a template polynucleotide sequence in an amplification reaction. As will be understood in the art, one primer in the primer pair is complementary to the template polynucleotide sequence (e.g., one primer is complementary to the 3' end of the template polynucleotide sequence) and the second primer of the primer pair is complementary to the first strand product synthesized in an amplification reaction from the first primer (e.g., the second primer is complementary to the 3' end of the first strand product synthesized from the first primer). The appropriate length of a primer depends on the intended use of the primer, but typically ranges from about 5 to about 100; from about 5 to about 75; from about 5 to about 50; from about 10 to about 35; from about 18 to about 22 nucleotides. A primer need not be the exact complementary sequence of the template sequence, but it should be sufficiently complementary to hybridize to the template sequence. The primer that is hybridized to the template sequence can initiate primer extension under appropriate conditions, as will be appreciated by a person of skill in the art. Conditions for the primer extension activity of a wide range of polymerase enzymes are known in the art.

In one aspect of the invention, provided is a microarray comprising a plurality of oligonucleotide primer pairs, wherein each oligonucleotide primer pair comprises a first oligonucleotide primer and a second oligonucleotide primer. The first oligonucleotide primer and a second oligonucleotide primer of a primer pair are located at the same discrete location on a microarray (see, e.g., FIG. 3). Each primer comprises at least one cleavable linkage for releasing the primer from the microarray. A "cleavable linkage" or "scissile linkage" is a linkage in the oligonucleotide that permits the specific cleavage of the oligonucleotide. For example, a succinate linkage could be used (see, e.g., U.S. published patent application 2006/0035218). In a preferred embodiment the cleavable linkage can be cleaved under mild, non-denaturing conditions leaving a 3' OH or 3' phosphate group. As will be understood by the person of skill in the art, a 3' phosphate group can be converted into a 3' OH group with a variety of phosphatases. In one embodiment, the cleavable linkage is selected from the group consisting of a 5' phosphorothiolate linkage, a disulfide bond, a 3' phosphorothiolate linkage and a deoxyuridine.

As will be appreciated by the person of skill in the art, the conditions under which an oligonucleotide is cleaved depends on which cleavable linkage is present. Oligonucleotides comprising a phosphothiolate linkage are described in U.S. application Ser. No. 60/694,783, filed on Jun. 28, 2005, the teachings of which are incorporated herein by reference in their entirety. A phosphorothiolate linkage (3' or 5') in a polynucleotide sequence can be efficiently cleaved according to methods known in the art (see, e.g., Vyle, et al., Biochemistry 31: 3012-3018 (1992); Sontheimer, et al., Methods 18: 29-37(1999); Mag, et al., Nucleic Acids Res., 19(7):1437-1441 (1991)). For example, a phosphorothiolate linkage can be cleaved chemically by exposure to particular metal agents, e.g., silver (Ag), mercury (Hg), copper (Cu), manganese (Mn), zinc (Zn) or cadmium (Cd), among others. Water-soluble salts that provide the anions of these metals are also useful. In addition, Iodine (I) can be used to cleave a phosphorothiolate linkage. Silver-containing salts such as silver nitrate ($AgNO_3$), or other salts that provide silver ions (Ag+), are particularly useful in the methods of the present invention.

Suitable conditions for cleaving a phosphorothiolate linkage include, but are not limited to, incubation with Ag+ ions at a pH in the range of from about 4.0 to about 10.0, from about 5.0 to about 9.0 or from about 6.0 to about 8.0, and at a temperature in the range of from about 15° C. to about 50° C., from about 20° C. to about 45° C., from about 25° C. to about 40° C., from about 22° C. to about 37° C., or from about 24° C. to about 32° C. Particular suitable conditions include, for example, incubation in the presence of 50 mM $AgNO_3$ at about 22° C. to about 37° C. for at least about 10 minutes at a pH of about 7.0.

An oligonucleotide comprising a disulfide bond can be cleaved using methods that are standard in the art, e.g., using a reducing agent such as beta mercaptoethanol, dithiothreitol, sodium 2-mercaptoethane sulfonate, or TCEP.

An oligonucleotide comprising a deoxyuridine can be cleaved enzymatically with Uracil DNA glycosylase (UDG) and an apyrimidinic (AP) lyase using methods that are standard in the art, e.g., using the USER™ (Uracil-Specific Excision Reagent; New England Biolabs), and/or a mixture of Uracil DNA glycosylase (UDG) and the DNA glycosylaselyase Endonuclease VIII. UDG catalyses the excision of a uracil base, forming an abasic (apyrimidinic or AP) site while leaving the phosphodiester backbone intact (see, e.g., Lindhal, et al., (1997) J. Biol. Chem., 252, 3286-3294 and Lindhal, (1982) Annu. Rev. Biochem., 51, 61-64). The lyase activity of Endonuclease VIII breaks (cleaves) the phosphodiester backbone at the 3' and 5' sides of the abasic site so that base-free deoxyribose is released (see, e.g., Melamede, et al., (1994) Biochemistry, 33, 1255-1264 and Jiang, et al., (1997) J. Biol. Chem., 272, 32230-32239).

The present invention also provides a microarray comprising a plurality of oligonucleotides which are attached to the microarray surface. Each oligonucleotide comprises (a) at least two primer nucleic acid sequences; (b) a first cleavable linkage which is located at or near the microarray surface, wherein cleaving the first cleavable linkage separates the oligonucleotide from the microarray surface; and (c) a second cleavable linkage located between the two primer nucleic acid sequences in each oligonucleotide, wherein cleaving the second cleavable linkage separates the two primer nucleic acid sequences in the oligonucleotide to produce an oligonucleotide primer pair. A cleavable linkage that is located at or near the microarray surface is a linkage that directly links the oligonucleotide to the microarray surface, and thus, is attached to the first nucleotide at the end of an oligonucleotide, or the cleavable linkage is located near the microarray surface, and thus, is a linkage in the oligonucleotide that is close to the end of the oligonucleotide that is attached to the microarray surface. For example, a cleavable linkage that is located near the microarray surface can be located within about 1 to about 15 nucleotides, within about 1 to about 10 nucleotides or within about 1 to about 5 nucleotides to the end of the oligonucleotide that is attached to the microarray surface.

In a particular embodiment, at least one oligonucleotide primer in each oligonucleotide primer pair comprises a target-specific nucleotide sequence. A "target-specific nucleotide sequence" is a nucleotide sequence which is complementary to the nucleotide sequence of a target polynucleotide. A "target polynucleotide" can be any polynucleotide, for example, genomic DNA, one or more exons of a gene, a complementary DNA (cDNA) sequence, RNA, intron sequences and the like. In a particular embodiment, at least one oligonucleotide primer in each oligonucleotide primer pair optionally comprises a universal nucleic acid sequence. A "universal nucleic acid sequence" (also referred to herein as a universal primer binding site) is a sequence that is a generally known sequence or commonly used nucleic acid sequence, as will be understood by a person of skill in the art. For example, the universal nucleic acid sequence can be P1, P2, SP6, T7 or an M13 sequence.

In another particular embodiment, at least one oligonucleotide primer in each oligonucleotide primer pair further comprises an affinity tag. An "affinity tag" is a tag or a label that permits the identification, capture and/or isolation of any agent that is attached to the affinity tag. Examples of an affinity tag include biotin, digoxigenin, a hapten, a ligand, a peptide and a nucleic acid. In a particular embodiment, the affinity tag is biotin. In a particular embodiment, the affinity tag is located at the 5' terminus of an oligonucleotide. An affinity tag that is located "at the 5' terminus" of an oligonucleotide includes an affinity tag on the first nucleotide at the 5' end of an oligonucleotide, or the affinity tag can be on a nucleotide that is near the 5' end of an oligonucleotide, e.g., within about 1 to about 15 nucleotides, within about 1 to about 10 nucleotides or within about 1 to about 5 nucleotides, from the 5' end of an oligonucleotide.

In a particular embodiment, the oligonucleotide primer pairs on a microarray described herein are used in an amplification reaction. As used herein, "amplification" or an "amplification reaction" refers to methods for amplification of a nucleic acid sequence including polymerase chain reaction (PCR), ligase chain reaction (LCR), rolling circle amplification (RCA), strand displacement amplification (SDA) and multiple displacement amplification (MDA), as will be understood by a person of skill in the art. Such methods for amplification comprise, e.g., primers that anneal to the nucleic acid sequence to be amplified, a DNA polymerase, and nucleotides. Furthermore, amplification methods, such as PCR, can be solid-phase amplification, polony amplification, colony amplification, emulsion PCR, bead RCA, surface RCA, surface SDA, etc., as will be recognized by one of skill in the art. It will also be recognized that it is advantageous to use an amplification method that results in exponential amplification of free DNA molecules in solution or tethered to a suitable matrix by only one end of the DNA molecule. Methods that rely on bridge PCR, where both PCR primers are attached to a surface (see, e.g., WO/18957 and Adessi et al., Nucleic Acids Research (2000): 28(20): E87) result in only linear amplification, which does not produce sufficient amounts of product to support efficient library construction for subsequent sequencing. Furthermore, the products of bridge PCR technologies are array-bound, and would have to be cleaved from the support as intact double stranded DNA molecules to be useful for subsequent sequencing. In addition, it will be recognized that it is often advantageous to use amplification protocols that maximize the fidelity of the amplified products to be used as templates in DNA sequencing procedures. Such protocols use, for example, DNA polymerases with strong discrimination against misincorporation of incorrect nucleotides and/or strong 3' exonuclease activities (also referred to as proofreading or editing activities) to remove misincorporated nucleotides during polymerization.

In a particular embodiment, a microarray of the present invention comprises at least about 100, 1000, 10,000, 100,000, 250,000 or 500,000 distinct elements (also referred to herein as discrete locations or features), wherein each element comprises one oligonucleotide primer of a primer pair, both oligonucleotide primers of a primer pair, or a plurality of oligonucleotides. In one embodiment, each element of the microarray has an area that is at least about 1, at least about 5, at least about 10, at least about 16, at least about 50 or at least about 100 square microns.

Also provided herein is a method for producing a microarray comprising a plurality of oligonucleotide primer pairs, wherein each oligonucleotide primer pair is synthesized at a discrete location on the microarray and the oligonucleotide primer pair comprises a first primer and a second primer. As will be understood in the art, methods for making an array having a single oligonucleotide nucleic acid sequence at a single feature on a microarray are known in the art (see, e.g., U.S. Pat. Nos. 5,445,934, 5,744,305, and 5,677,195, which describe methods using light-directed spatially parallel chemical synthesis of oligonucleotides, and Nuwaysir, et al.,
(Genome Research (2002) 12: 1749-1755) and U.S. Pat. No. 6,375,903, which describe oligonucleotide arrays produced by maskless photolithography using a Maskless Array Synthesizer (MAS) instrument (NimbleGen Systems, Inc.); the teachings of all of which are herein incorporated by reference in their entirety). In a particular embodiment of the present invention, the first primer and second primer each comprise at least one cleavable linkage. The method for producing a microarray of the present invention comprises providing a microarray which comprises a plurality of discrete locations, and each discrete location comprises a first primer synthesis site and a second primer synthesis site. Each second primer synthesis site is capped with a blocking group to prevent primer synthesis at the second primer synthesis site and the first primers comprising at least one cleavable linkage are synthesized at each first primer synthesis site on the microarray, which produces a plurality of first primers on the microarray. The plurality of first primers are capped to prevent further synthesis of each first primer. Each second primer synthesis site is uncapped and a second primer comprising at least one cleavable linkage is synthesized at each second primer synthesis site on the microarray, which produces a plurality of second primers on the microarray. Methods of using multiple protecting groups are known in the art. For example, Kwiatkowski et al. (Nucleic Acids Research (1999) 27: 4710-4714) describe levulinyl-protected phosphoramidites (TEG-O-Lev) used in concert with a methylamino-derivatized surface. In this example, the phosphoramide linkage is stable under conditions of oligonucleotide synthesis and ammoniacal deprotection, but is cleaved by aqueous acetic acid. As a result oligonucleotides linked to the array with the traditional base-cleavable linkage can be synthesized on an array which also has methylamino-derivatized surface coupled via a TEG phosphoramide linkage. Once the first oligonucleotide primer synthesis is completed, the second oligonucleotide can be synthesized on the hydroxyl group protected by the TEG-O-Lev amidite. The TEG-O-Lev protected hydroxyl group is deprotected by with hydrazine. As will be appreciated by a person of skill in the art, other combination of hydroxyl protecting groups can be used to achieve the desired results (e.g., see "Protective groups in Organic Synthesis" Greene & Wuts, (1991) $2^{nd}$ Ed., Wiley & Sons, NY). Thus, the present invention provides a method for producing a microarray, wherein a plurality of oligonucleotide primer pairs are synthesized at discrete locations on the microarray, in addition the present invention provides a microarray produced by the described method.

Another aspect of the present invention is a method for capturing a plurality of oligonucleotide primer pairs on a capturing means in a capturing support, wherein each oligonucleotide primer pair is captured at a discrete location on the capturing support. In one embodiment, the plurality of oligonucleotide primer pairs are captured in the capturing support at discrete locations that correspond to the discrete locations of the oligonucleotide primers on a microarray. A "capturing support" is any suitable support that can capture an oligonucleotide and retain the oligonucleotide at a discrete location corresponding to the discrete location the oligonucleotide was present at on a microarray. For example, a capturing support can be a semi-solid medium, e.g., a polyacrylamide gel. In a particular embodiment, the polyacrylamide gel is a reversible polyacrylamide gel. A reversible polyacrylamide gel can be de-polymerized using a suitable reagent, e.g., by periodate cleavage of a DATD crosslinker. In a particular embodiment, the capturing support comprises a capturing means for capturing the oligonucleotide primer pairs. A capturing means can capture an oligonucleotide, e.g., by capturing an affinity tag that is present on the oligonucleotide. In one embodiment, the capturing means comprise a plurality of magnetic beads. In a particular embodiment, the magnetic beads are each at least about 0.5 microns in diameter. Capturing means and methods of using same are known in the art, e.g., U.S. Pat. No. 6,534,262, U.S. Pat. No. 5,705,628 and U.S. Pat. No. 5,898,071, the teachings of which are herein incorporated by reference in their entirety.

In another particular embodiment, the magnetic beads comprise an agent that binds to an affinity tag present on at least one primer. Thus, in one embodiment at least one oligonucleotide primer in each primer pair further comprises an affinity tag. In a particular embodiment, the affinity tag is biotin, digoxigenin, a hapten, a ligand, a peptide or a nucleic acid. In another particular embodiment, the oligonucleotide comprises biotin and the magnetic beads comprise avidin or streptavidin for capturing an oligonucleotide comprising biotin.

The method for capturing a plurality of oligonucleotide primer pairs on a capturing means in a capturing support, wherein each oligonucleotide primer pair is captured at a discrete location on the capturing support comprises embedding each oligonucleotide primer pair present at a discrete location on a microarray into a capturing support, wherein each oligonucleotide primer on a microarray comprises at least one first cleavable linkage. The oligonucleotide primer pairs are captured from the microarray in the capturing support by the capturing means. The oligonucleotide primer pairs are separated from the microarray by cleaving the at least one first cleavable linkage in each oligonucleotide primer. Thus, the oligonucleotide primer pairs are captured in the capturing support and the discrete locations of the oligonucleotide primer pairs which were present on the microarray are maintained in the capturing support on the capturing means. In one embodiment, the microarray is removed from the capturing support after embedding the microarray and cleaving the oligonucleotides.

In a further embodiment, the capturing means comprising an oligonucleotide primer pair are contacted with a target nucleic acid sequence. In one embodiment, contacting the oligonucleotide primer pair with a target nucleic acid sequence occurs under conditions in which the target nucleic acid sequence hybridizes to one of more of the oligonucleotide primers. Hybridization is the annealing of complementary nucleic acid sequences under appropriate conditions, as will be appreciated by a person of skill in the art. In a particular embodiment, the method further comprises amplifying the target nucleic acid sequence that is hybridized to at least one primer in the oligonucleotide primer pair, thereby producing an amplified target nucleic acid sequence. In one particular embodiment, the amplification reaction is an emulsion polymerase chain reaction. In another particular embodiment, the amplified target nucleic acid sequence is sequenced.

In another embodiment, the capturing means comprising an oligonucleotide primer pair is isolated from the capturing support before or after contacting the oligonucleotide primer pair with a target nucleic acid sequence. Isolating the capturing means from the capturing support can be achieved by any known method. For example, a capturing support that is a reversible polyacrylamide gel can be depolymerized with periodate, thereby permitting the separation of the capturing means from the capturing support.

In an additional embodiment, the capturing means comprising an oligonucleotide primer pair and a target nucleic acid sequence that has been hybridized to at least one oligonucleotide on the capturing means is isolated from the capturing support before amplifying the target nucleic acid sequence.

In another particular embodiment, at least a portion of at least one oligonucleotide primer in each oligonucleotide primer pair further comprises a second cleavable linkage, wherein the second cleavable linkage is different from the first cleavable linkage. Thus, in one embodiment, the second cleavable linkage of at least a portion of at least one oligonucleotide primer in each oligonucleotide primer pair is cleaved, thereby producing a capturing support comprising a plurality of oligonucleotide primer pairs, wherein at least a portion of at least one oligonucleotide primer in each oligonucleotide primer pair is liberated from the capturing means in the capturing support. Under these conditions, at least one oligonucleotide primer in a primer pair is captured on a capturing means, and at least a portion of the other primer in the primer pair is liberated or released from the capturing means. In a further embodiment, at least a portion of both oligonucleotide primers in the primer pair are released from the capturing means by cleaving a cleavable linkage in the primer. Cleavage of at least a portion of at least one primer in an oligonucleotide primer pair promotes local amplification (e.g., in a PCR amplification) of a target nucleic acid sequence in the capturing support or in an emulsion amplification reaction. For example, by incorporating a percentage of uridine instead of a thymidine at the 5' end of one of the oligonucleotides, the oligonucleotide can be cleaved enzymatically from the beads to promote local PCR. Additionally, a small proportion of uridine/thymidine at a similar position in the other oligonucleotide of the oligonucleotide primer pair can also be incorporated to release a portion of that oligonucleotide as well.

In a further embodiment, at least one oligonucleotide primer in each oligonucleotide primer pair further comprises a polymerizable group. For example, the polymerizable group can be ACRYDITE™, acrylamide, acrylic acid, vinyl, or other suitable unsaturated moiety that can be co-polymerized into a polyacrylamide gel. The addition of a polymerizable group to an oligonucleotide allows immobilization of the oligonucleotide in a polyacrylamide capturing support, thereby limiting diffusion of the oligonucleotide and thus, limiting diffusion of an amplification product incorporating the oligonucleotide.

In another aspect of the invention, provided is a method for capturing a plurality of oligonucleotide primer pairs on a capturing support, wherein each oligonucleotide primer pair comprises a first primer and a second primer, each primer comprises at least one cleavable linkage, and wherein each first primer is captured from a first microarray and each second primer is captured from a second microarray. The method comprises embedding a first microarray comprising a plurality of first primers, wherein each first primer is located on the first microarray at a discrete location, into a capturing support under conditions in which each of the first primers are captured in the capturing support and the discrete location of each of the first primers is maintained in the capturing support. The first primers are separated from the first microarray by cleaving the at least one first cleavable linkage in the first primers. The first microarray is removed from the capturing support and a second microarray comprising a plurality of second primers, wherein each second primer is located on the second microarray at a discrete location, is embedded into the capturing support under conditions in which each of the second primers are captured in the capturing support and the discrete location of each of the second primers is maintained in the capturing support, and wherein the discrete location of each of the second primers overlaps with the discrete location of each of the first primers. The second primers are separated from the second microarray by cleaving the at least one second cleavable linkage in each of the second primers, thereby capturing a plurality of oligonucleotide primer pairs on a capturing support, wherein each oligonucleotide primer pair comprises a first primer and a second primer, and wherein each first primer is captured from a first microarray and each second primer is captured from a second microarray.

In one embodiment, the second microarray is removed from the capturing support after the second primers have been separated from the second microarray. In a particular embodiment, the capturing support further comprises a capturing means. In a further embodiment, the method further comprises contacting the plurality of oligonucleotide primer pairs on the capturing support and/or on the capturing means with a target nucleic acid sequence, and amplifying the target nucleic acid sequence in an amplification reaction, thereby producing a plurality of amplified target nucleic acid sequences. In a particular embodiment, the amplified target nucleic acid sequences are sequenced. In another embodiment, at least a portion of at least one oligonucleotide primer in each oligonucleotide primer pair further comprises a third cleavable linkage, wherein the third cleavable linkage is different from the first and second cleavable linkage. In a particular embodiment, the method further comprises cleaving at least a portion of the third cleavable linkage of at least one oligonucleotide primer in each oligonucleotide primer pair, thereby producing a capturing support comprising a plurality of oligonucleotide primer pairs, wherein at least a portion of at least one oligonucleotide primer in each oligonucleotide primer pair is liberated from the capturing means in the capturing support. Thus, in one embodiment, the method further comprises contacting the capturing support comprising a plurality of oligonucleotide primer pairs with a target nucleic acid sequence, and amplifying said target nucleic acid sequence in an amplification reaction, thereby producing an amplified target nucleic acid sequence. In one embodiment, the amplified target nucleic acid sequence is sequenced.

In another aspect of the invention, provided is a method for amplifying a target polynucleotide, comprising a) providing a plurality of oligonucleotide primer pairs, wherein each oligonucleotide primer pair is located at a discrete position on a microarray, and wherein each oligonucleotide primer in each oligonucleotide primer pair comprises at least one cleavable linkage; b) hybridizing a target polynucleotide to at least one primer in at least one oligonucleotide primer pair on the microarray, thereby producing a microarray comprising at least one primer pair comprising at least one primer hybridized to a target polynucleotide; c) embedding the microarray of step b) into a capturing support; d) separating the at least one primer oligonucleotide pair comprising at least one primer hybridized to a target polynucleotide from the microarray by cleaving the at least one cleavable linkage in each primer, thereby releasing the at least one oligonucleotide primer pair comprising at least one primer hybridized to a target polynucleotide from the microarray, wherein the at least one oligonucleotide primer pair comprising at least one primer hybridized to a target polynucleotide is captured in the capturing support; and e) amplifying the target polynucleotide under conditions in which the at least one oligonucleotide primer pair comprising at least one primer hybridized to the target polynucleotide amplifies the target polynucleotide by polymerase chain reaction, whereby an amplified target polynucleotide is produced, thereby amplifying a target polynucleotide. In one embodiment, each oligonucleotide primer further comprises at the 5' end of the oligonucleotide primer a restriction endonuclease recognition site for a distally cleaving restriction endonuclease. As used herein, "a distally cleaving restriction endonuclease" refers to a restriction endonuclease that recognizes a particular site within a nucleic acid sequence and cleaves this nucleic acid sequence outside the region of the recognition site (cleavage occurs at a site which is distal or outside the site recognized by the restriction endonuclease). In one embodiment, a restriction endonuclease that cleaves a nucleic acid distally to its restriction endonuclease recognition site cleaves on one side of the restriction endonuclease recognition site (for example, upstream or downstream of the recognition site). In another embodiment, restriction endonuclease that cleaves a nucleic acid distally to its restriction endonuclease recognition site cleaves on both sides of the restriction endonuclease recognition site (for example, upstream and downstream of the recognition site). In another embodiment, the restriction endonuclease cleaves once between two restriction endonuclease recognition sites. In one embodiment, a distally cleaving restriction endonuclease is a Type IIs or a Type III restriction endonuclease. Thus, in one embodiment, the method further comprises cleaving the amplified target polynucleotide with a restriction endonuclease specific for the restriction endonuclease recognition site, thereby producing a fragment of the amplified target polynucleotide, wherein at least a portion of the oligonucleotide primer sequence is removed.

In one particular aspect of the invention, a pair of sequencing adapters are joined to the fragment of the amplified target polynucleotide, such that a sequencing adapter is joined to each end of the fragment, and wherein each sequencing adapter comprises a primer binding site, thereby producing an adapter-modified target polynucleotide. As used herein, "joining" refers to methods such as ligation, annealing or recombination used to attach one component to another. In one embodiment, the adapter-modified target polynucleotide is sequenced. In a particular embodiment, the pair of sequencing adapters is a pair of asymmetrical adapters. Asymmetrical adapters are described in detail in U.S. application Ser. No. 11/338,620, filed on Jan. 26, 2006, the teachings of which are incorporated herein by reference in their entirety. In one embodiment, a pair of asymmetrical adapters comprise:

a) a first oligonucleotide adapter selected from the group consisting of:
   (i) an asymmetrical tail adapter comprising a first ligatable end, and a second end comprising a single-stranded 3' overhang of at least about 8 nucleotides;
   (ii) an asymmetrical Y adapter comprising a first ligatable end, and a second unpaired end comprising two non-complementary strands, wherein the length of the non-complementary strands are at least about 8 nucleotides; and
   (iii) an asymmetrical bubble adapter comprising an unpaired region of at least about 8 nucleotides flanked on each side by a paired region;

and b) a second oligonucleotide adapter selected from the group consisting of:
   (i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
   (ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

wherein the nucleic acid sequence of the first and second asymmetrical adapters are not identical.

As used herein, two (or more) asymmetrical adapters are "non-identical" or "not identical" when the asymmetrical adapters differ from each other by at least one nucleotide in a primer binding site, by at least one nucleotide in the complementary nucleic acid sequence of a primer binding site, and/or by the presence or absence of a blocking group. An asymmetrical adapter comprises a primer binding site in a region of single-stranded nucleic acid sequence in the asymmetrical adapter. The two (or more) non-identical asymmetrical adapters can have substantial differences in nucleic acid sequences. For example, two asymmetrical tail adapters, asymmetrical bubble adapters or two asymmetrical Y adapters can comprise entirely different sequences (e.g., with little or no sequence identity). In a particular embodiment, the non-identical asymmetrical adapters have little or no sequence identity in the unpaired region (e.g., the tail region, the arms of the Y region, or the bubble region). Alternatively, a pair of asymmetrical adapters are not identical such that they differ in kind or type, e.g., the first and second asymmetrical adapters are not both asymmetrical tail adapters, not both asymmetrical Y adapters, or not both asymmetrical bubble adapters. That is, a pair of asymmetrical adapters can comprise, e.g., an asymmetrical tail adapter and a bubble adapter or Y adapter, or a pair of asymmetrical adapters can comprise a bubble and a Y adapter. In a particular embodiment, two (or more) asymmetrical adapters that are not identical in kind or type differ from each other by at least one nucleotide in a primer binding site, by at least one nucleotide in the complementary nucleic acid sequence of a primer binding, and/or by the presence or absence of a blocking group.

In an alternative aspect of the invention, a universal adapter is joined to each end of the amplified target polynucleotide, wherein each universal adapter comprises a primer binding site, and the 3' end of each universal adapter comprises a restriction endonuclease recognition site for a distally cleaving restriction endonuclease, thereby producing a first adapter-modified target polynucleotide. As used herein, a "universal adapter" is an adapter that comprises a universal primer binding site. As described above, A "universal primer binding site" (also referred to herein as a universal nucleic acid sequence) is a sequence that is a generally known sequence or commonly used nucleic acid sequence, as will be understood by a person of skill in the art. For example, the universal nucleic acid sequence can be an M13 sequence. In one embodiment, the method further comprises amplifying the first adapter-modified target polynucleotide, thereby producing an amplified adapter-modified target polynucleotide. In a particular embodiment, the method further comprises cleaving the amplified adapter-modified target polynucleotide with a restriction endonuclease specific for the restriction endonuclease recognition site, thereby producing a fragment of the amplified adapter-modified target polynucleotide, wherein at least a portion of the universal adapter sequence is removed. In a further particular embodiment, a pair of sequencing adapters are joined to the fragment of the amplified adapter-modified target polynucleotide, wherein one sequencing adapter is joined to each end of the fragment, and wherein each sequencing adapter comprises a primer binding site, thereby producing a second adapter-modified target polynucleotide. Thus, in another embodiment of the invention, the method further comprises sequencing the second adapter-modified target polynucleotide. In a particular embodiment, the pair of sequencing adapters is a pair of asymmetrical adapters.

In a still further alternative embodiment of the method for amplifying a target polynucleotide, each oligonucleotide primer further comprises a restriction endonuclease recognition site for a distally cleaving restriction endonuclease, and at least one oligonucleotide primer in the oligonucleotide primer pair further comprises a universal primer sequence. In a particular embodiment, the capturing support further comprises a primer that is identical to the universal primer sequence in the at least one oligonucleotide primer. In one embodiment, the primer that is identical to the universal primer sequence further comprises a polyacrylamide group. In a further embodiment, the method further comprises amplifying the target polynucleotide under conditions in which at least one oligonucleotide primer and the primer that is identical to the universal primer sequence amplifies the target polynucleotide by polymerase chain reaction, thereby producing an amplified target polynucleotide. In a particular embodiment, the method further comprises cleaving the amplified target polynucleotide with a restriction endonuclease specific for the restriction endonuclease recognition site to produce a fragment of the amplified target polynucleotide, wherein at least a portion of the oligonucleotide primer sequences are removed. In a further embodiment, the method further comprises joining a pair of sequencing adapters to the fragment of the amplified target polynucleotide to produce an adapter-modified target polynucleotide, such that one sequencing adapter is joined to each end of the fragment. Each sequencing adapter comprises a primer binding site. In one embodiment, the adapter-modified target polynucleotide is sequenced. In a particular embodiment, the pair of sequencing adapters is a pair of asymmetrical adapters.

In a still further alternative embodiment of the invention, the method of amplifying a target polynucleotide comprises joining to the ends of the amplified target polynucleotide a pair of asymmetrical adapters, wherein the first and second asymmetrical adapters further comprise a restriction endonuclease recognition site for a distally cleaving restriction endonuclease, and wherein the nucleic acid sequence of the first and second asymmetrical adapters are not identical, thereby producing a first adapter-modified target polynucleotide. In a particular embodiment, the method further comprises amplifying the first adapter-modified target polynucleotide, thereby producing an amplified adapter-modified target polynucleotide. In one embodiment, the amplified adapter-modified target polynucleotide is cleaved with a restriction endonuclease specific for the restriction endonuclease recognition site, thereby producing a fragment of the amplified adapter-modified target polynucleotide, wherein at least a portion of the asymmetrical adapter sequences are removed. In a further embodiment, a pair of sequencing adapters are joined to the fragment of the amplified adapter-modified target polynucleotide, wherein one sequencing adapter is joined to each end of the fragment, and wherein each sequencing adapter comprises a primer binding site, thereby producing a second adapter-modified target polynucleotide. Thus, in one embodiment, the method further comprises sequencing the second adapter-modified target polynucleotide. In one embodiment, the pair of sequencing adapters is a pair of asymmetrical adapters.

In one embodiment, the oligonucleotide primers are synthesized on the microarray in the conventional 3'-down orientation. In another embodiment, the oligonucleotide primers are synthesized in the 5'-down orientation.

In a particular embodiment, a target polynucleotide hybridized to an oligonucleotide primer on the array is copied by extension of the 3' hydroxyl of one oligonucleotide primer using DNA polymerase and deoxynucleoside triphosphates. The hybridized target polynucleotide can be released by chemical or thermal denaturation and discarded before proceeding with the embedding in a capturing support, or alternatively, the double-stranded primer extension product is cleaved after embedding in a capturing support by treatment with a restriction endonuclease. Thus, in one embodiment of the invention, only a single cleavable primer sequence is required at each microarray element, and a universal adapter is used to provide the second primer nucleic acid sequence required for subsequent PCR. In this embodiment, the oligonucleotide primers of the array are attached to the microarray surface at their 5' ends. Methods to produce such arrays are well known in the art, e.g., by ink jet deposition of oligonucleotides having a reactive group at the 5' end or by light-directed array synthesis methods using 5'-O-phosphoramidites. A cleavable linkage is incorporated at or near the attachment site at the 5' end of each oligonucleotide primer on the microarray. The nucleic acid sequence of the oligonucleotide primers located at each element of the microarray is designed such that extension of the primers produces a first strand extension product comprising the target polynucleotide. The target polynucleotide can then be further characterized, e.g., by DNA sequencing. For example, genomic DNA from a sample to be analyzed can be randomly sheared to an appropriate size range (e.g., at least about 300 base pairs to at least about 1000 base pairs). The fragments can be blunt-ended and ligated to an excess of universal adapters comprising a universal primer site or universal primer binding site, thereby producing adapter-ligated fragments. The adapter-ligated fragments can be optionally gel-purified to produce a collection of adapter-ligated fragments of homogeneous size range and distribution (e.g., approximately 500 bp, +50 bp), and/or to remove excess adapters. The adapter-ligated fragments are hybridized to the oligonucleotide primers on the microarray, preferably under stringent hybridization conditions and excess unhybridized fragments, or weakly hybridized fragments, are optionally removed using high stringency wash conditions. The 3' ends of microarray oligonucleotide primers that are hybridized to a complementary nucleic acid sequence of adapter-ligated fragments are extended, e.g., by addition of DNA polymerase and deoxynucleoside triphosphates (dNTPs) to generate an array-bound complementary first strand extension product of each hybridized adapter-ligated fragment. The hybridized fragments can be removed or released from the array and discarded. Typical conditions for removing hybridized fragments include washing at approximately 95° C. in a stripping solution having low ionic strength, which may also include formamide, urea, or other denaturant, or in a stripping solution having an extreme pH (above about pH 11 or below about pH 2.5). The array is rinsed to remove the stripping solution, coated with a capturing support, such as a semisolid matrix (e.g., a polyacrylamide gel) to embed the array-bound first strand extension products and the microarray primers. The microarray-bound first strand extension products and microarray primers are cleaved to liberate (release) them from the microarray surface and into the capturing support. Amplification, e.g., PCR, reagents including a DNA polymerase, dNTPs and a universal primer complementary to the primer nucleic acid sequence in the first strand extension products (produced by extension of the oligonucleotide primer through the universal adapter sequence) are added in an appropriate buffer and amplification is performed in each discrete location in the capturing support using the liberated microarray primers and the universal primer, resulting in a plurality of amplified target polynucleotide sequences in the capturing support (see FIG. 7A).

In an alternative embodiment, the microarray oligonucleotide primers comprise a cleavable linkage but which are not cleaved and liberated from the microarray immediately after embedding in the capturing support (see FIG. 7B). Amplification is carried out in the capturing support in the presence of a universal primer. Specifically, the amplification products (e.g., double-stranded amplification products) are generated in discrete locations in the capturing support using the microarray primer and a universal primer. The amplification products are all tethered to the microarray surface by one DNA strand via a microarray primer. The double-stranded amplification products can then be cleaved and liberated from the microarray by cleaving the cleavable linkage in the microarray primer. In one embodiment, the cleavable linkage is a restriction endonuclease recognition site and the double-stranded PCR products are cleaved and liberated from the microarray by cleavage with a restriction endonuclease that recognizes the restriction endonuclease recognition site. In a still further embodiment, the restriction endonuclease recognition site is recognized by a distally cleaving restriction endonuclease, wherein the distally cutting restriction endonuclease will cleave within the target polynucleotide sequence thereby liberating the amplified target polynucleotide products from the microarray and removing the microarray primers from the target polynucleotide sequence at the same time. In a still further embodiment the universal primer also comprises a restriction endonuclease recognition site that is recognized by a distally cleaving restriction endonuclease and is which oriented in such a way that cleavage using a distally cutting restriction endonuclease will cleave within the target sequence just beyond the end of the primer. This allows both primers to be removed from the double-stranded target sequence at the same time as they are being liberated from the microarray.

In an alternative embodiment, the universal primers for amplification comprise a polymerizable moiety (e.g., ACRYDITE™ or acrylamide) at or near their 5' ends. The universal primers are added prior to polymerization of the capturing support, e.g., a polyacrylamide gel, such that the universal primers are immobilized in the capturing support after polymerization. Amplifying a target polynucleotide with an immobilized primer produces an immobilized amplified target polynucleotide. In one embodiment, the universal primer comprises a recognition site for a distally cutting restriction endonuclease at or near the 5' end, wherein cleavage using a distally cutting restriction endonuclease will cut within the target sequence, e.g., just beyond the end of the universal primer sequence. This permits the immobilized amplified target polynucleotide products generated after amplification to be cleaved and released from the capturing support for subsequent collection and characterization, while simultaneously removing the universal primer sequence.

In embodiments where restriction endonuclease cleavage is used, it will be understood by one skilled in the art that it is advantageous to treat the starting genomic DNA with a site-specific DNA methylase that is capable of blocking cleavage of the corresponding restriction endonuclease cleavage sites within the target genomic sequences. A wide variety of methylases have been described, including those that block cleavage by multiple endonucleases (e.g., CpG methylase) and those that block cleavage by endonucleases that cleave distally to their recognition sites. For example, MmeI and EcoP15I sites are not cleaved after methylation of their recognition sites by the corresponding methyltransferases or methyltransferase subunits (Rao et al., 2005, BBRC, 334: 803; Tucholski et al., 1998, Gene, 223: 293). By methylating the recognition sites in the target genomic DNA, cleavage will only occur at sites within, or adjacent to the recognition sites within the primer sequences.

In an additional aspect of the invention, the method for amplifying a target nucleic acid sequence further comprises removing nucleic acid sequences that are not target sequences for amplification from a pool of nucleic acid sequences (e.g., a whole genome), by hybridizing the nucleic acid sequences to a microarray. The microarray comprises oligonucleotides that bind to nucleic acid sequences that are not target nucleic acid sequences (e.g., repetitive DNA elements such as Alu elements). Hybridization of the pool of nucleic acid sequences to the microarray will selectively remove those nucleic acid sequences that are not target nucleic acid sequences for amplification. The remaining nucleic acid sequences is then enriched for target nucleic acid sequences and can be hybridized to a microarray with oligonucleotide primer pairs specific for the target nucleic acid sequences. Amplification of the target nucleic acid sequences is performed in any one of the methods already described. Alternatively, a microarray can be used to enrich for sequence fragments that specifically hybridize to the array, while allowing all other (non-specific) sequences to be removed or washed away.

The relevant teachings of all the references, patents and patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for amplifying a target polynucleotide, comprising:
   a) providing a plurality of oligonucleotide primer pairs, wherein each oligonucleotide primer pair is located at a discrete position on a microarray, and wherein each oligonucleotide primer in each oligonucleotide primer pair comprises at least one cleavable linkage;
   b) hybridizing a target polynucleotide to at least one primer in at least one oligonucleotide primer pair on the microarray, thereby producing a microarray comprising at least one primer pair comprising at least one primer hybridized to a target polynucleotide;
   c) embedding the microarray of step b) into a capturing support;
   d) separating the at least one primer oligonucleotide pair comprising at least one primer hybridized to a target polynucleotide from the microarray by cleaving the at least one cleavable linkage in each primer, thereby releasing the at least one oligonucleotide primer pair comprising at least one primer hybridized to a target polynucleotide from the microarray, wherein the at least one oligonucleotide primer pair comprising at least one primer hybridized to a target polynucleotide is captured in the capturing support; and
   e) amplifying the target polynucleotide under conditions in which the at least one oligonucleotide primer pair comprising at least one primer hybridized to the target polynucleotide amplifies the target polynucleotide by polymerase chain reaction, whereby an amplified target polynucleotide is produced;
   thereby amplifying a target polynucleotide.

2. The method of claim 1, wherein each oligonucleotide primer further comprises at the 5' end of the oligonucleotide primer a restriction endonuclease recognition site for a distally cleaving restriction endonuclease.

3. The method of claim 2, wherein the distally cleaving restriction endonuclease is a Type IIs or a Type III restriction endonuclease.

4. The method of claim 2, further comprising cleaving the amplified target polynucleotide with a restriction endonuclease specific for the restriction endonuclease recognition site, thereby producing a fragment of the amplified target polynucleotide, wherein at least a portion of the oligonucleotide primer sequence is removed.

5. The method of claim 4, further comprising joining a pair of sequencing adapters to the fragment of the amplified target polynucleotide, wherein one sequencing adapter is joined to each end of the fragment, and wherein each sequencing adapter comprises a primer binding site, thereby producing an adapter-modified target polynucleotide.

6. The method of claim 5, further comprising sequencing the adapter-modified target polynucleotide.

7. The method of claim 5, wherein the pair of sequencing adapters is a pair of asymmetrical adapters, and wherein said pair of asymmetrical adapters comprise:
   a) a first oligonucleotide adapter selected from the group consisting of:
      (i) an asymmetrical tail adapter comprising a first ligatable end, and a second end comprising a single-stranded 3' overhang of at least about 8 nucleotides;
      (ii) an asymmetrical Y adapter comprising a first ligatable end, and a second unpaired end comprising two non-complementary strands, wherein the length of the non-complementary strands are at least about 8 nucleotides; and
      (iii) an asymmetrical bubble adapter comprising an unpaired region of at least about 8 nucleotides flanked on each side by a paired region;
   and
   b) a second oligonucleotide adapter selected from the group consisting of:
      (i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
      (ii) an asymmetrical Y adapter comprising a first ligatable end, and a second unpaired end comprising two non-complementary strands, wherein the length of the non-complementary strands are at least about 8 nucleotides; and
      (iii) an asymmetrical bubble adapter comprising an unpaired region of at least about 8 nucleotides flanked on each side by a paired region;
   wherein the nucleic acid sequence of the first and second asymmetrical adapters are not identical.

8. The method of claim 1, further comprising joining a universal adapter to each end of the amplified target polynucleotide, wherein each universal adapter comprises a primer binding site, and the 3' end of each universal adapter comprises a restriction endonuclease recognition site for a distally cleaving restriction endonuclease, thereby producing a first adapter-modified target polynucleotide.

9. The method of claim 8, further comprising amplifying the first adapter-modified target polynucleotide, thereby producing an amplified adapter-modified target polynucleotide.

10. The method of claim 9, further comprising cleaving the amplified adapter-modified target polynucleotide with a restriction endonuclease specific for the restriction endonuclease recognition site, thereby producing a fragment of the amplified adapter-modified target polynucleotide, wherein at least a portion of the universal adapter sequence is removed.

11. The method of claim 10, further comprising joining a pair of sequencing adapters to the fragment of the amplified adapter-modified target polynucleotide, wherein one sequencing adapter is joined to each end of the fragment, and wherein each sequencing adapter comprises a primer binding site, thereby producing a second adapter-modified target polynucleotide.

12. The method of claim 11, further comprising sequencing the second adapter-modified target polynucleotide.

13. The method of claim 11, wherein the pair of sequencing adapters is a pair of asymmetrical adapters, and wherein said pair of asymmetrical adapters comprise:
  a) a first oligonucleotide adapter selected from the group consisting of:
    (i) an asymmetrical tail adapter comprising a first ligatable end, and a second end comprising a single-stranded 3' overhang of at least about 8 nucleotides;
    (ii) an asymmetrical Y adapter comprising a first ligatable end, and a second unpaired end comprising two non-complementary strands, wherein the length of the non-complementary strands are at least about 8 nucleotides; and
    (iii) an asymmetrical bubble adapter comprising an unpaired region of at least about 8 nucleotides flanked on each side by a paired region;
  and
  b) a second oligonucleotide adapter selected from the group consisting of:
    (i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
    (ii) an asymmetrical Y adapter comprising a first ligatable end, and a second unpaired end comprising two non-complementary strands, wherein the length of the non-complementary strands are at least about 8 nucleotides; and
    (iii) an asymmetrical bubble adapter comprising an unpaired region of at least about 8 nucleotides flanked on each side by a paired region;
  wherein the nucleic acid sequence of the first and second asymmetrical adapters are not identical.

14. The method of claim 1, wherein each oligonucleotide primer further comprises a restriction endonuclease recognition site for a distally cleaving restriction endonuclease, and wherein at least one oligonucleotide primer in the oligonucleotide primer pair further comprises a universal primer sequence.

15. The method of claim 14, wherein the distally cleaving restriction endonuclease is a Type IIs or a Type III restriction endonuclease.

16. The method of claim 14, wherein the capturing support further comprises a primer that is identical to the universal primer sequence.

17. The method of claim 14, wherein the primer that is identical to the universal primer sequence further comprises a polyacrylamide group.

18. The method of claim 17, further comprising amplifying the target polynucleotide under conditions in which the primer that is identical to the universal primer sequence amplifies the target polynucleotide by polymerase chain reaction, thereby producing an amplified target polynucleotide.

19. The method of claim 14, further comprising cleaving the amplified target polynucleotide with a restriction endonuclease specific for the restriction endonuclease recognition site, thereby producing a fragment of the amplified target polynucleotide, wherein at least a portion of the oligonucleotide primer sequences are removed.

20. The method of claim 19, further comprising joining a pair of sequencing adapters to the fragment of the amplified target polynucleotide, wherein one sequencing adapter is joined to each end of the fragment, and wherein each sequencing adapter comprises a primer binding site, thereby producing an adapter-modified target polynucleotide.

21. The method of claim 20, further comprising sequencing the adapter-modified target polynucleotide.

22. The method of claim 20, wherein the pair of sequencing adapters is a pair of asymmetrical adapters, and wherein said pair of asymmetrical adapters comprise:
  a) a first oligonucleotide adapter selected from the group consisting of:
    (i) an asymmetrical tail adapter comprising a first ligatable end, and a second end comprising a single-stranded 3' overhang of at least about 8 nucleotides;
    (ii) an asymmetrical Y adapter comprising a first ligatable end, and a second unpaired end comprising two non-complementary strands, wherein the length of the non-complementary strands are at least about 8 nucleotides; and
    (iii) an asymmetrical bubble adapter comprising an unpaired region of at least about 8 nucleotides flanked on each side by a paired region;
  and
  b) a second oligonucleotide adapter selected from the group consisting of:
    (i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;
    (ii) an asymmetrical Y adapter comprising a first ligatable end, and a second unpaired end comprising two non-complementary strands, wherein the length of the non-complementary strands are at least about 8 nucleotides; and
    (iii) an asymmetrical bubble adapter comprising an unpaired region of at least about 8 nucleotides flanked on each side by a paired region;
  wherein the nucleic acid sequence of the first and second asymmetrical adapters are not identical.

23. The method of claim 1, further comprising joining to the ends of the amplified target polynucleotide a pair of asymmetrical adapters, wherein said pair of asymmetrical adapters comprise:
  a) a first oligonucleotide adapter selected from the group consisting of:
    (i) an asymmetrical tail adapter comprising a first ligatable end, and a second end comprising a single-stranded 3' overhang of at least about 8 nucleotides;
    (ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

and b) a second oligonucleotide adapter selected from the group consisting of:

(i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;

(ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

wherein the first and second asymmetrical adapters further comprise a restriction endonuclease recognition site for a distally cleaving restriction endonuclease, and wherein the nucleic acid sequence of the first and second asymmetrical adapters are not identical, thereby producing a first adapter-modified target polynucleotide.

24. The method of claim 23, further comprising amplifying the first adapter-modified target polynucleotide, thereby producing an amplified adapter-modified target polynucleotide.

25. The method of claim 24, further comprising cleaving the amplified adapter-modified target polynucleotide with a restriction endonuclease specific for the restriction endonuclease recognition site, thereby producing a fragment of the amplified adapter-modified target polynucleotide, wherein at least a portion of the asymmetrical adapter sequences are removed.

26. The method of claim 25, further comprising joining a pair of sequencing adapters to the fragment of the amplified adapter-modified target polynucleotide, wherein one sequencing adapter is joined to each end of the fragment, and wherein each sequencing adapter comprises a primer binding site, thereby producing a second adapter-modified target polynucleotide.

27. The method of claim 26, further comprising sequencing the second adapter-modified target polynucleotide.

28. The method of claim 26, wherein the pair of sequencing adapters is a pair of asymmetrical adapters, and wherein said pair of asymmetrical adapters comprise:

a) a first oligonucleotide adapter selected from the group consisting of:

(i) an asymmetrical tail adapter comprising a first ligatable end, and a second end comprising a single-stranded 3' overhang of at least about 8 nucleotides;

(ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

and b) a second oligonucleotide adapter selected from the group consisting of:

(i) an asymmetrical tail adapter comprising a first ligatable end, and a second end comprising a single-stranded 5' overhang of at least about 8 nucleotides, wherein the 3' end of the strand that does not comprise the 5' overhang comprises at least one blocking group;

(ii) an asymmetrical Y adapter comprising a first ligatable end, and a second unpaired end comprising two non-complementary strands, wherein the length of the non-complementary strands are at least about 8 nucleotides; and (iii) an asymmetrical bubble adapter comprising an unpaired region of at least about 8 nucleotides flanked on each side by a paired region;

wherein the nucleic acid sequence of the first and second asymmetrical adapters are not identical.

29. The method of claim 1, wherein the at least one target polynucleotide is a fragment of a genomic DNA.

30. The method of claim 29, wherein the fragment of a genomic DNA comprises at least about 1000 nucleotides.

31. The method of claim 1, wherein the capturing support support is a polyacrylamide gel.

32. The method of claim 31, wherein the polyacrylamide gel is a reversible polyacrylamide gel.

33. A method for amplifying a target polynucleotide, comprising:

a) providing an oligonucleotide primer located at a discrete position on a microarray, wherein the oligonucleotide primer comprises at least one cleavable linkage;

b) hybridizing a target polynucleotide to the oligonucleotide primer on the microarray, wherein the target polynucleotide comprises a universal adapter ligated to each end of the target polynucleotide, and wherein each universal adapter comprises a universal primer sequence, thereby producing a microarray comprising an oligonucleotide primer hybridized to a target polynucleotide;

c) extending the oligonucleotide primer hybridized to the target polynucleotide, thereby producing a first strand primer extension product located at a discrete location on the microarray;

d) removing the target polynucleotide from the first strand primer extension product located at a discrete location on the microarray;

e) embedding the first strand primer extension product located at a discrete location on the microarray into a capturing support, wherein the capturing support comprises a universal primer;

f) amplifying the target polynucleotide in the capturing support under conditions in which the oligonucleotide primer hybridized to the target polynucleotide and the universal primer amplifies the target polynucleotide by polymerase chain reaction, whereby an amplified target polynucleotide is produced;

thereby amplifying a target polynucleotide.

34. The method of claim 33, further comprising cleaving oligonucleotide primer on the microarray after amplifying the target polynucleotide in the capturing support, thereby releasing the amplified target polynucleotide from the microarray.

35. The method of claim 33, wherein the oligonucleotide primer further comprises a restriction endonuclease recognition site for a distally cleaving restriction endonuclease.

36. The method of claim 35, wherein the distally cleaving restriction endonuclease is a Type IIs or a Type III restriction endonuclease.

37. The method of claim 35, further comprising cleaving the oligonucleotide primer with a restriction endonuclease specific for the restriction endonuclease recognition site after amplifying the target polynucleotide in the capturing support, thereby producing a fragment of the amplified target polynucleotide, wherein at least a portion of the oligonucleotide primer sequence is removed.

38. The method of claim 33, further comprising cleaving oligonucleotide primer on the microarray before amplifying the target polynucleotide in the capturing support, thereby releasing the oligonucleotide primer from the microarray.

39. The method of claim 31, wherein at least one of the primers in the at least one oligonucleotide primer pair includes a polymerizable group that can co-polymerize into the polyacrylamide gel.

* * * * *